United States Patent
Hashimshony et al.

(10) Patent No.: US 7,899,515 B2
(45) Date of Patent: Mar. 1, 2011

(54) ELECTROMAGNETIC SENSORS FOR TISSUE CHARACTERIZATION

(75) Inventors: Dan Hashimshony, Givat Ada (IL); Gil Cohen, Jerusalem (IL); Iddo Geltner, Herzlia (IL)

(73) Assignee: Dune Medical Devices Ltd., Caesaria (IL)

( * ) Notice: Subject to any disclaimer, the term of this patent is extended or adjusted under 35 U.S.C. 154(b) by 530 days.

(21) Appl. No.: 11/887,571

(22) PCT Filed: Mar. 29, 2006

(86) PCT No.: PCT/IL2006/000392

§ 371 (c)(1), (2), (4) Date: Sep. 28, 2007

(87) PCT Pub. No.: WO2006/103665

PCT Pub. Date: Oct. 5, 2006

(65) Prior Publication Data

US 2009/0062637 A1 Mar. 5, 2009

Related U.S. Application Data

(60) Provisional application No. 60/665,842, filed on Mar. 29, 2005.

(51) Int. Cl.
*A61B 5/05* (2006.01)

(52) U.S. Cl. .................................. 600/407; 600/409

(58) Field of Classification Search .............. 600/9, 600/407; 422/82.01
See application file for complete search history.

(56) References Cited

U.S. PATENT DOCUMENTS 3,830,224 A 8/1974 Vanzetti et al.

(Continued)

FOREIGN PATENT DOCUMENTS

DE 19705260 A1 8/1997

(Continued)

OTHER PUBLICATIONS

Communication Pursuant to Article 94(3) EPC Dated Oct. 7, 2009 From the European Patent Office Re.: Application No. 06728196.4.

(Continued)

*Primary Examiner* — Eric F Winakur
*Assistant Examiner* — Michael T Rozanski

(57) ABSTRACT

A sensor for tissue characterization is provided, comprising: a resonator, configured to be placed proximally to an edge of a tissue for characterization, without penetrating the tissue, the resonator comprising a conductive structure associated with a diameter-equivalent dimension D, in a plane substantially parallel with the edge, and with a feature size d; and at least one conductive lead, for providing communication with an external system, wherein the resonator is configured to resonate at a frequency which corresponds to a free-air wavelength range of between about lambda and about 40 lambda, wherein lambda is at least about ten times the diameter-equivalent D, and wherein upon receiving a signal in the range of between about lambda and about 40 lambda, the sensor is configured to induce electric and magnetic fields, in a near zone, in the tissue, the near zone having a diameter of about D, so that the tissue in the near zone effectively functions as part of the resonator, influencing its resonating values, and so the tissue in the near zone is thereby characterized by its electromagnetic properties, by the resonating response of the resonator.

26 Claims, 14 Drawing Sheets
(9 of 14 Drawing Sheet(s) Filed in Color)

U.S. PATENT DOCUMENTS

| | | | |
|---|---|---|---|
| 4,291,708 A | 9/1981 | Frei et al. |
| 4,344,440 A | 8/1982 | Aaby et al. |
| 4,458,694 A | 7/1984 | Sollish et al. |
| 4,537,203 A | 8/1985 | Machida |
| 4,539,640 A | 9/1985 | Fry et al. |
| RE32,000 E | 10/1985 | Sagi |
| 4,617,939 A | 10/1986 | Brown et al. |
| 4,625,171 A | 11/1986 | Sekihara et al. |
| 4,682,594 A | 7/1987 | Mok |
| 4,689,567 A | 8/1987 | Maudsley |
| 4,751,464 A | 6/1988 | Bridges |
| 4,768,513 A | 9/1988 | Suzuki |
| 4,779,624 A | 10/1988 | Yokoi |
| 4,785,806 A | 11/1988 | Deckelbaum |
| 5,115,137 A | 5/1992 | Andersson-Engels et al. |
| 5,143,079 A | 9/1992 | Frei et al. |
| 5,227,730 A | 7/1993 | King et al. |
| 5,277,730 A | 1/1994 | Darsey et al. |
| 5,334,941 A | 8/1994 | King |
| 5,383,454 A | 1/1995 | Bucholz |
| 5,442,290 A | 8/1995 | Crooks |
| 5,482,041 A | 1/1996 | Wilk et al. |
| 5,482,047 A | 1/1996 | Nordgren et al. |
| 5,558,092 A | 9/1996 | Unger et al. |
| 5,572,132 A | 11/1996 | Pulyer et al. |
| 5,630,426 A | 5/1997 | Eggers et al. |
| 5,678,565 A | 10/1997 | Sarvazyan |
| 5,699,804 A | 12/1997 | Rattner |
| 5,704,355 A | 1/1998 | Bridges |
| 5,727,569 A | 3/1998 | Benetti et al. |
| 5,735,278 A | 4/1998 | Hoult et al. |
| 5,744,971 A | 4/1998 | Chan et al. |
| 5,758,646 A | 6/1998 | Van Der Meulen et al. |
| 5,800,350 A | 9/1998 | Coppleson et al. |
| 5,807,257 A | 9/1998 | Bridges |
| 5,810,742 A | 9/1998 | Pearlman |
| 5,821,410 A | 10/1998 | Xiang et al. |
| 5,829,437 A | 11/1998 | Bridges et al. |
| 5,884,239 A | 3/1999 | Romanik, Jr. |
| 5,900,618 A | 5/1999 | Anlage et al. |
| 5,927,284 A | 7/1999 | Borst et al. |
| 6,004,263 A | 12/1999 | Nakaichi et al. |
| 6,010,455 A | 1/2000 | Barnett et al. |
| 6,026,323 A | 2/2000 | Skladnev et al. |
| 6,055,451 A | 4/2000 | Bambot et al. |
| 6,055,452 A | 4/2000 | Pearlman |
| 6,061,589 A | 5/2000 | Bridges et al. |
| 6,071,239 A | 6/2000 | Cribbs et al. |
| 6,081,738 A | 6/2000 | Hinohara et al. |
| 6,086,534 A | 7/2000 | Kesten |
| 6,090,041 A | 7/2000 | Clark et al. |
| 6,109,270 A | 8/2000 | Mah et al. |
| 6,135,968 A | 10/2000 | Brounstein |
| 6,167,297 A | 12/2000 | Benaron |
| 6,173,604 B1 | 1/2001 | Xiang et al. |
| 6,203,533 B1 | 3/2001 | Ouchi |
| 6,233,479 B1 | 5/2001 | Haddad et al. |
| 6,258,576 B1 | 7/2001 | Richards-Kortum et al. |
| 6,280,704 B1 | 8/2001 | Schutt et al. |
| 6,287,302 B1 | 9/2001 | Berube |
| 6,308,097 B1 | 10/2001 | Pearlman |
| 6,315,981 B1 | 11/2001 | Unger |
| 6,321,106 B1 | 11/2001 | Lemelson |
| 6,331,166 B1 | 12/2001 | Burbank et al. |
| 6,370,426 B1 | 4/2002 | Campbell et al. |
| 6,375,634 B1 | 4/2002 | Carroll |
| 6,377,841 B1 | 4/2002 | Lin et al. |
| 6,380,747 B1 | 4/2002 | Goldfine et al. |
| 6,397,095 B1 | 5/2002 | Eyuboglu et al. |
| 6,405,733 B1 | 6/2002 | Fogarty et al. |
| 6,411,103 B1 | 6/2002 | Tobias et al. |
| 6,500,112 B1 | 12/2002 | Khouri |
| 6,530,944 B2 | 3/2003 | West et al. |
| 6,544,185 B2 | 4/2003 | Montegrande |
| 6,546,787 B1 | 4/2003 | Schiller et al. |
| 6,564,806 B1 | 5/2003 | Fogarty et al. |
| 6,592,520 B1 | 7/2003 | Peszynski et al. |
| 6,597,185 B1 | 7/2003 | Talanov et al. |
| 6,671,540 B1 | 12/2003 | Hochman |
| 6,677,755 B2 | 1/2004 | Belt et al. |
| 6,695,782 B2 | 2/2004 | Ranucci et al. |
| 6,699,206 B2 | 3/2004 | Burbank et al. |
| 6,722,371 B1 | 4/2004 | Fogarty et al. |
| 6,728,565 B2 | 4/2004 | Wendlandt |
| 6,741,077 B2 | 5/2004 | Yokoyama et al. |
| 6,747,454 B2 | 6/2004 | Belt |
| 6,752,154 B2 | 6/2004 | Fogarty et al. |
| 6,766,185 B2 | 7/2004 | Scott |
| 6,813,515 B2 | 11/2004 | Hashimshony |
| 6,064,081 A1 | 1/2005 | Hashimshony |
| 6,840,948 B2 | 1/2005 | Albrecht et al. |
| 6,909,084 B2 | 6/2005 | Tachi et al. |
| 6,936,003 B2 | 8/2005 | Iddan |
| 6,962,587 B2 | 11/2005 | Johnson et al. |
| 7,082,325 B2 | 7/2006 | Hashimshony et al. |
| 7,184,824 B2 | 2/2007 | Hashimshony |
| 2001/0051774 A1 | 12/2001 | Littrup et al. |
| 2002/0055754 A1 | 5/2002 | Ranucci et al. |
| 2002/0059938 A1 | 5/2002 | Fogarty et al. |
| 2002/0068880 A1 | 6/2002 | Burbank et al. |
| 2002/0120265 A1 | 8/2002 | Fowler |
| 2003/0036674 A1 | 2/2003 | Bouton |
| 2003/0045798 A1 | 3/2003 | Hular et al. |
| 2003/0062897 A1 | 4/2003 | Belt et al. |
| 2003/0117140 A1 | 6/2003 | Belt et al. |
| 2003/0138378 A1 | 7/2003 | Hashimshony |
| 2003/0146814 A1 | 8/2003 | Wiltshire |
| 2003/0163037 A1 | 8/2003 | Bladen et al. |
| 2003/0171664 A1 | 9/2003 | Wendlandt |
| 2003/0187347 A1 | 10/2003 | Nevo et al. |
| 2003/0187366 A1 | 10/2003 | Hashimshony |
| 2003/0199753 A1 | 10/2003 | Hibner et al. |
| 2003/0216648 A1 | 11/2003 | Lizzi et al. |
| 2003/0229343 A1 | 12/2003 | Albrecht et al. |
| 2004/0065158 A1 | 4/2004 | Schrepfer et al. |
| 2004/0168692 A1 | 9/2004 | Fogarty et al. |
| 2004/0254457 A1 | 12/2004 | Van der Weide |
| 2005/0010131 A1 | 1/2005 | Burbank et al. |
| 2005/0021019 A1 | 1/2005 | Hashimshony et al. |
| 2005/0107717 A1 | 5/2005 | Yamamoto et al. |
| 2006/0253107 A1 | 11/2006 | Hashimshony et al. |
| 2006/0264738 A1 | 11/2006 | Hashimshony et al. |
| 2007/0032739 A1 | 2/2007 | Hashimshony et al. |
| 2007/0032747 A1 | 2/2007 | Hashimshony et al. |
| 2007/0179397 A1 | 8/2007 | Hashimshony et al. |
| 2007/0255169 A1 | 11/2007 | Hashimshony et al. |
| 2007/0260156 A1 | 11/2007 | Hashimshony |
| 2008/0021343 A1 | 1/2008 | Hashimshony et al. |
| 2008/0039742 A1 | 2/2008 | Hashimshony et al. |
| 2008/0154090 A1 | 6/2008 | Hashimshony |
| 2008/0287750 A1 | 11/2008 | Hashimshony et al. |

FOREIGN PATENT DOCUMENTS

| | | |
|---|---|---|
| DE | 19734978 A1 | 2/1999 |
| EP | 419235 | 3/1991 |
| GB | 01153980 | 3/1968 |
| JP | 2003-516214 | 5/2003 |
| WO | WO 97/12553 | 4/1997 |
| WO | WO 01/42807 | 6/2001 |
| WO | WO 01/43630 | 6/2001 |
| WO | WO 01/65240 | 9/2001 |
| WO | WO 02/32335 | 4/2002 |
| WO | WO 02/058531 | 8/2002 |

| WO | WO 03/009752 | 2/2003 |
| WO | WO 03/060462 | 7/2003 |
| WO | WO 2005/009200 | 2/2005 |
| WO | WO 2005/089065 | 9/2005 |
| WO | WO 2006/072947 | 7/2006 |
| WO | WO 2006/092797 | 9/2006 |
| WO | WO 2007/015255 | 2/2007 |
| WO | WO 2007/083310 | 7/2007 |
| WO | WO 2008/132714 | 11/2008 |
| WO | WO 2008/132750 | 11/2008 |

OTHER PUBLICATIONS

International Preliminary Report on Patentability Dated Nov. 12, 2009 From the International Bureau of WIPO Re.: Application No. PCT/IL2008/000406.
Official Action Dated Aug. 27, 2009 From the US Patent and Trademark Office Re.: U.S. Appl. No. 11/705,143.
Official Action Dated Aug. 27, 2009 From the US Patent and Trademark Office Re.: U.S. Appl. No. 11/797,167.
Official Action Dated Oct. 27, 2009 From the US Patent and Trademark Office Re.: U.S. Appl. No. 11/487,431.
Official Action Dated Aug. 31, 2009 From US Patent and Trademark Office Re.: U.S. Appl. No. 11/797,166.
Response Dated Oct. 13, 2009 to Official Action of Sep. 15, 2009 From the US Patent and Trademark Office Re.: U.S. Appl. No. 11/196,732.
Response Dated Oct. 13, 2009 to Official Action of Dec. 18, 2008 From the US Patent and Trademark Office Re.: U.S. Appl. No. 10/534,544.
Response Dated Nov. 25, 2009 to Official Action of Aug. 27, 2009 From the US Patent and Trademark Office Re.: U.S. Appl. No. 11/705,143.
Response Dated Nov. 25, 2009 to Official Action of Aug. 27, 2009 From the US Patent and Trademark Office Re.: U.S. Appl. No. 11/797,167.
Supplementary Partial European Search Report and the European Searching Opinion Dated Dec. 4, 2009 From the European Patent Office Re.: Application No. 06700052.1.
Translation of Office Action Dated Sep. 18, 2009 From the State Intellectual Property Office of the People's Republic of China Re.: Application No. 20068006513.7.
Examination Report Dated Nov. 18, 2008 From the Government of India, Patent Office Re.: Application No. 668/CHENP/2006.
International Search Report Dated Nov. 27, 2008 From the International Searching Authority Re.: Application No. PCT/IL2008/000406.
Translation of the Notice of Reason for Rejection Dated Oct. 31, 2008 From the Japanese Patent Office Re.: Application No. 2003-560509.
Written Opinion Dated Nov. 27, 2008 From the International Searching Authority Re.: Application No. PCT/IL2008/000406.
Brown "A Survey of Image Registration Techniques", ACM Computing Surveys, 24(4): 325-376, 1992.
Burdette et al. "In Vivo Probe Measurement Technique for Determining Dielectric Properties at VFW Through Microwave Frequencies", IEEE Transactions on Microwave Theory & Techniques, MTT-28(4): 414-427, 1980.
Misra et al. "Noninvasive Electrical Characterization of Materials at Microwave Frequencies Using an Open-Ended Coaxial Line: Test of an Improved Calibration Technique", IEEE Transactions on Microwave Theory & Techniques, 38(1): 8-13, 1990.
Mosig et al. "Reflection of an Open-Ended Coaxial Line", IEEE Transactions on Instrumentation & Measurement, IM-30(1): 46-51, 1981.
Rajshekhar "Continuous Impedence Monitoring During CT-Guided Stereotactic Surgery: Relative Value in Cystic and Solid Lesions", British Journal of Neurosurgery, 6: 439-444, 1992.
Schwan "Mechanism Responsible for Electrical Properties of Tissues and Cell Suspensions", Medical Process Through Technology, 19: 163-165, 1993.
Smith et al. "In Vivo Measurement of Tumor Conductiveness With the Magnetic Bioimpedance Method", IEEE Transactions on Biomedical Engineering, 47(10): 1403-1405, 2000.

Stuchly et al. "Measurement of Radio Frequency Permittivity of Biological Tissues With an Open-Ended Coaxial Line: Part II-Experimental Results", IEEE Transactions on Microwave Theory & Techniques, MTT-30(1): 87-91, 1982.
Surowiec et al. "Dielectric Properties of Breast Carcinoma and the Surrounding Tissues", IEEE Transactions on Biomedical Engineering, 35(4): 257-263, 1988.
Xu et al. "Measurement of Microwave Permittivity Using Open Ended Elliptical Coaxial Probes", IEEE Transactions on Microwave Theory & Techniques, 40(1): 143-150, 1992.
Communication Pursuant to Article 96(2) EPC Dated Aug. 10, 2006 From the European Patent Office Re.: Application No. 02795418.9.
Communication Pursuant to Article 96(2) EPC Dated Jan. 12, 2006 From the European Patent Office Re.: Application No. 02795418.9.
Communication Relating to the Results of the Partial International Search Dated Sep. 1, 2008 From the International Searching Authority Re.: Application No. PCT/IL2008/000406.
International Preliminary Report on Patentability Dated Feb. 4, 2008 From the International Preliminary Examining Authority Re.: Application No. PCT/IL06/00392.
International Preliminary Report on Patentability Dated Jan. 22, 2009 From the International Bureau of WIPO Re.: Application No. PCT/IL2006/000908.
International Preliminary Report on Patentability Dated Apr. 26, 2007 From the International Bureau of WIPO Re.: Application No. PCT/IL2005/000330.
International Preliminary Report on Patentatbility Dated Aug. 9, 2007 From the International Bureau of WIPO Re.: Applicaiton No. PCT/IL2006/000015.
Office Action Dated Feb. 11, 2009 From the Israeli Patent Office Re.: Application No. 173231 and Its Translation Into English.
Office Action Dated Nov. 18, 2008 From the Government of India, Patent Office Re.: Application No. 668/CHENP/2006.
Office Action Dated Mar. 20, 2009 From the State Intellectual Property Office of the People's Republic of China Re.: Application No. 200680019026.4.
Official Action Dated Apr. 1, 2008 From US Patent and Trademark Office Re.: U.S. Appl. No. 11/745,334.
Official Action Dated Jun. 3, 2005 From the US Patent and Trademark Office Re.: U.S. Appl. No. 10/891,750.
Official Action Dated Jun. 4, 2007 From the US Patent and Trademark Office Re.: U.S. Appl. No. 10/298,196.
Official Action DAted Jul. 9, 2008 From the US Patent and Trademark Office Re.: U.S. Appl. No. 11/196,732.
Official Action Dated Apr. 10, 2006 From the US Patent and Trademark Office Re.: U.S. Appl. No. 10/965,752.
Official Action Dated Feb. 10, 2006 From the US Patent and Trademark Office Re.: U.S. Appl. No. 10/298,196.
Official Action Dated Oct. 10, 2006 From the US Patent and Trademark Office Re.: U.S. Appl. No. 10/298,196.
Official Action Dated Nov. 19, 2007 From the US Patent and Trademark Office Re.: U.S. Appl. No. 11/196,732.
Official Action Dated Mar. 21, 2008 From the US Patent and Trademark Office Re.: U.S. Appl. No. 10/558,831.
Official Action Dated Jan. 24, 2008 From the US Patent and Trademark Office Re.: U.S. Appl. No. 10/298,196.
Response Dated Aug. 3, 2007 to Written Opinion of May 3, 2007 From the International Searching Authority Re.: Application No. PCT/IL06/00392.
Response Dated Jan. 4, 2007 to Communication Pursuant to Article 96(2) of Aug. 10, 2006 From the European Patent Office Re.: Application No. 02795418.9.
Response Dated Mar. 16, 2007 to Communication Pursuant to Article 96(2) EPC of Jan. 19, 2007 From the European Patent Office Re.: Application No. 02795418.9.
Supplementary European Search Report and the European Search Opinion Dated Jun. 5, 2009 From the European Patent Office Re.: Application No. 06728196.4.
Communication Pursuant to Article 94(3) EPC Dated Mar. 15, 2010 From the European Patent Office Re.: Application No. 06700052.1.
Examination Report Dated Nov. 18, 2008 From the Government of India, Patent Office Re.: Application No. 668/CHENP/2006.

International Search Report Dated Nov. 27, 2008 From the International Searching Authority Re.: Application No. PCT/IL2008/000406.

Notice of Allowance Dated Oct. 20, 2006 From the US Patent and Trademark Office Re.: U.S. Appl. No. 10/965,752.

Official Action Dated Jun. 3, 2005 From the US Patent and Trademark Office Re.: U.S. Appl. No. 10/891,750.

Official Action Dated Feb. 4, 2010 From the US Patent and Trademark Office Re.: U.S. Appl. No. 11/196,732.

Official Action Dated Mar. 11, 2010 From the US Patent and Trademark Office Re.: U.S. Appl. No. 11/797,166.

Official Action Dated Mar. 17, 1010 From the US Patent and Trademark Office Re.: U.S. Appl. No. 10/567,581.

Reponse Dated Mar. 1, 2010 to Official Action of Oct. 27, 2009 From the US Patent and Trademark Office Re.: U.S. Appl. No. 11/487,731.

Response Dated Jan. 3, 2010 to Office Action of Sep. 18, 2009 From the State Intellectual Property Office of the People's Republic of China Re.: Application No. 200680006513.7.

Response Dated Jan. 7, 2010 to Official Action of Dec. 7, 2009 From the US Patent and Trademark Office Re.: U.S. Appl. No. 11/797,167.

Response Dated Feb. 8, 2010 to Communication Pursuant to Article 94(3) EPC of Oct. 7, 2009 From the European Patent Office Re.: Application No. 06728196.4.

Response Dated Dec. 30, 2009 to Official Action of Aug. 31, 2009 From the US Patent and Trademark Office Re.: U.S. Appl. No. 11/797,166.

Translation of the Notice of Reason for Rejection Dated Oct. 31, 2008 From the Japanese Patent Office Re.: Application No. 2003-560509.

Written Opinion Dated Nov. 27, 2008 From the International Searching Authority Re.: Application No. PCT/IL2008/000406.

Official Action Dated Jul. 9, 2010 From the US Patent and Trademark Office Re.: U.S. Appl. No. 11/705,143.

Notice of Allowance Dated Jun. 29, 2010 From the US Patent and Trademark Office Re.: U.S. Appl. No. 11/487,431.

Response Dated Aug. 4, 2010 to Official Action of Feb. 4, 2010 From the US Patent and Trademark Office Re.: U.S. Appl. No. 11/196,732.

Translation of Notification to Grant Patent Right for Invention Dated Aug. 3, 2010 From the State Intellectual Property Office of the People's Republic of China Re.: Application No. 200680019026.4.

Notification to Grant Patent Right for Invention Dated Aug. 3, 2010 From the State Intellectual Property Office of the People's Republic of China Re.: Application No. 200680019026.4 and Its Translation Into English.

Response Dated Sep. 2, 2010 to Communication Pursuant to Article 94(3) EPC of Mar. 15, 2010 From the European Patent Office Re.: Application No. 06700052.1.

Response Dated Aug. 30, 2010 to Official Action of Mar. 11, 2010 From the US Patent and Trademark Officie Re.: U.S. Appl. No. 11/797,166.

Official Action Dated Aug. 31, 2010 From the US Patent and Trademark Office Re. U.S. Appl. No. 11/350,102.

Translation of Notice of Reason for Rejection Dated Aug. 24, 2010 From the Japanese Patent Office Re. Application No. 2006-520980.

Communication Pursuant to Article 94(3) EPC Dated Sep. 27, 2010 From the European Patent Office Re.: Application No. 06728196.4.

Response Dated Sep. 16, 2010 to Official Action of Mar. 17, 1010 From the US Patent and Trademark Office Re.: U.S. Appl. No. 10/567,581.

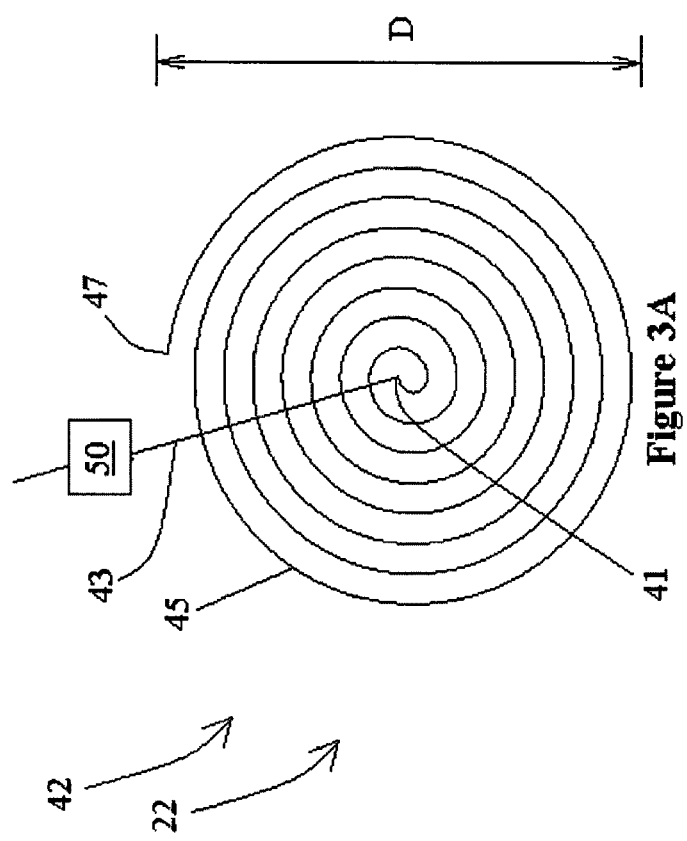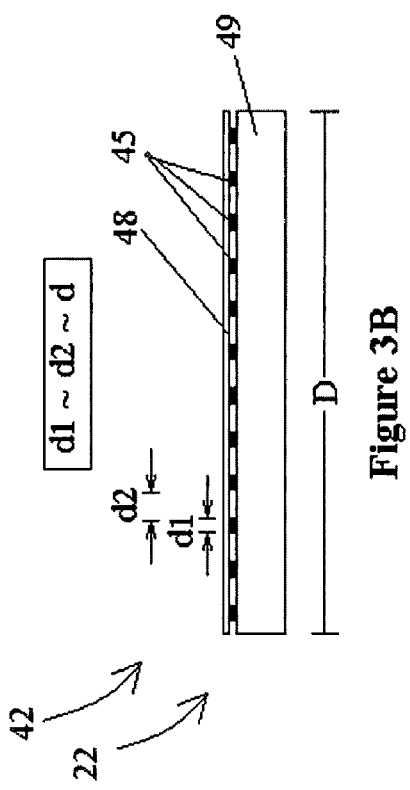

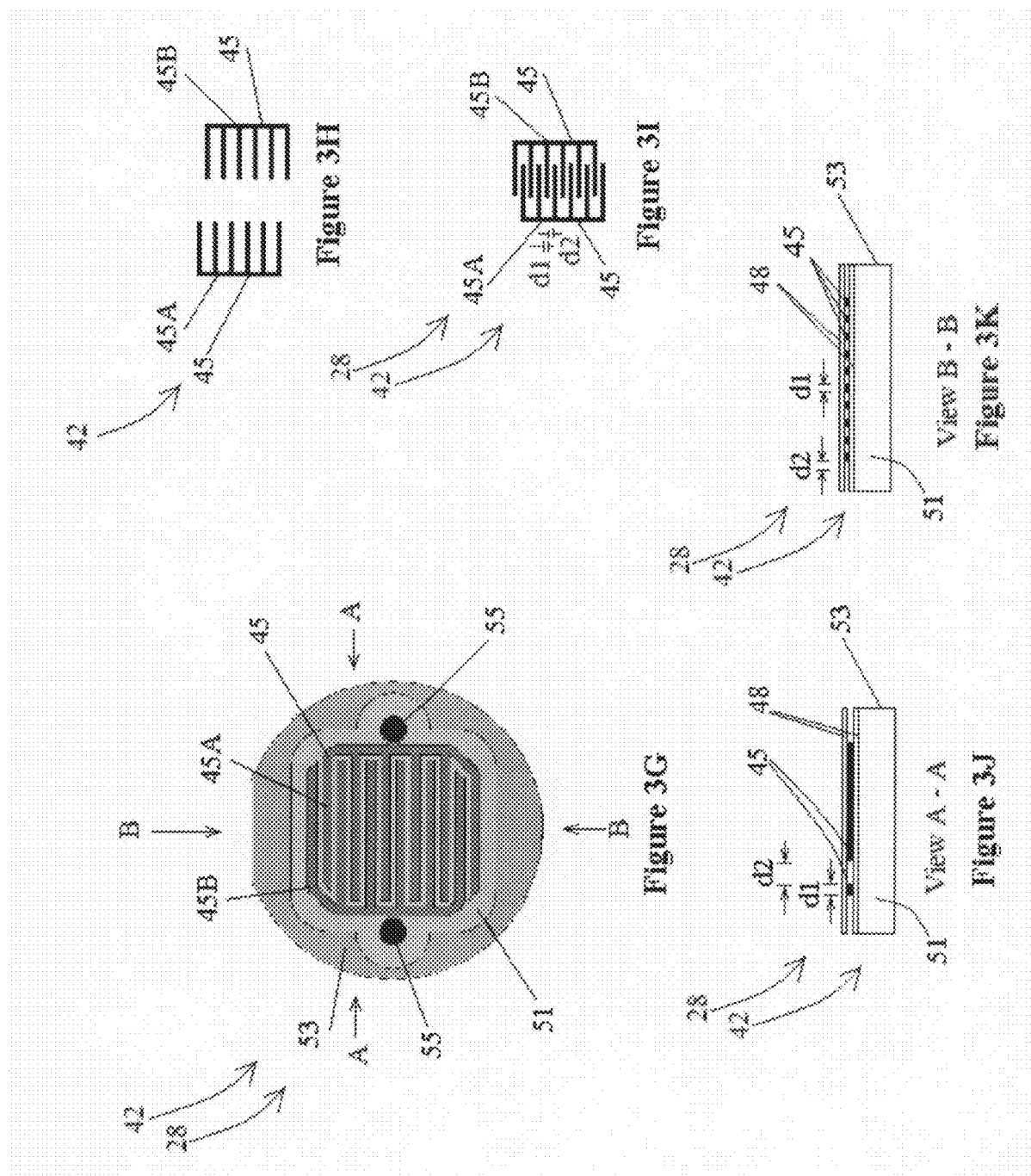

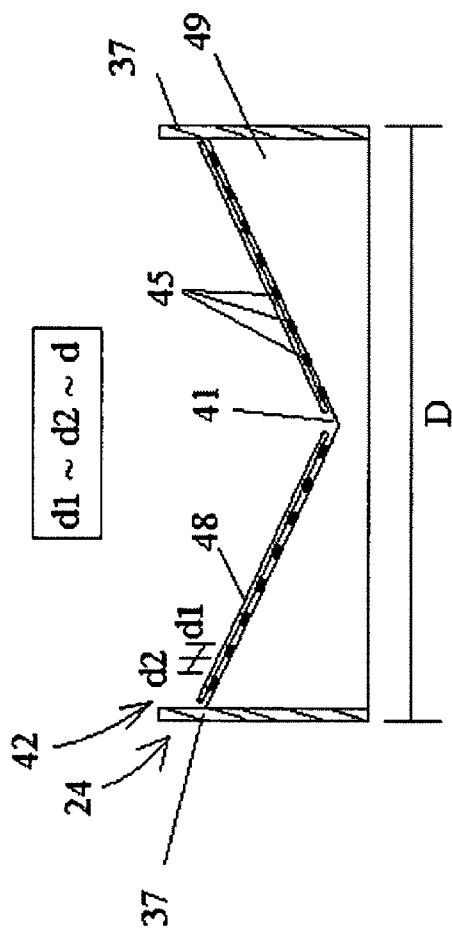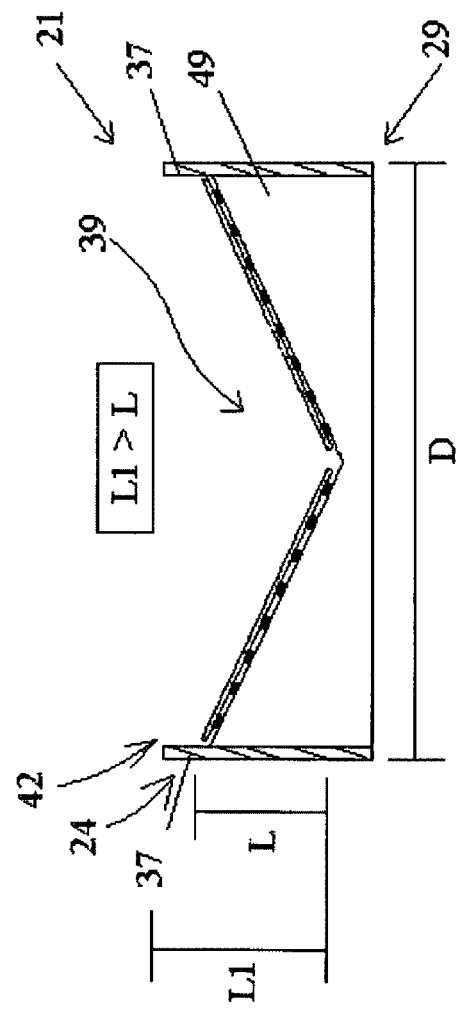

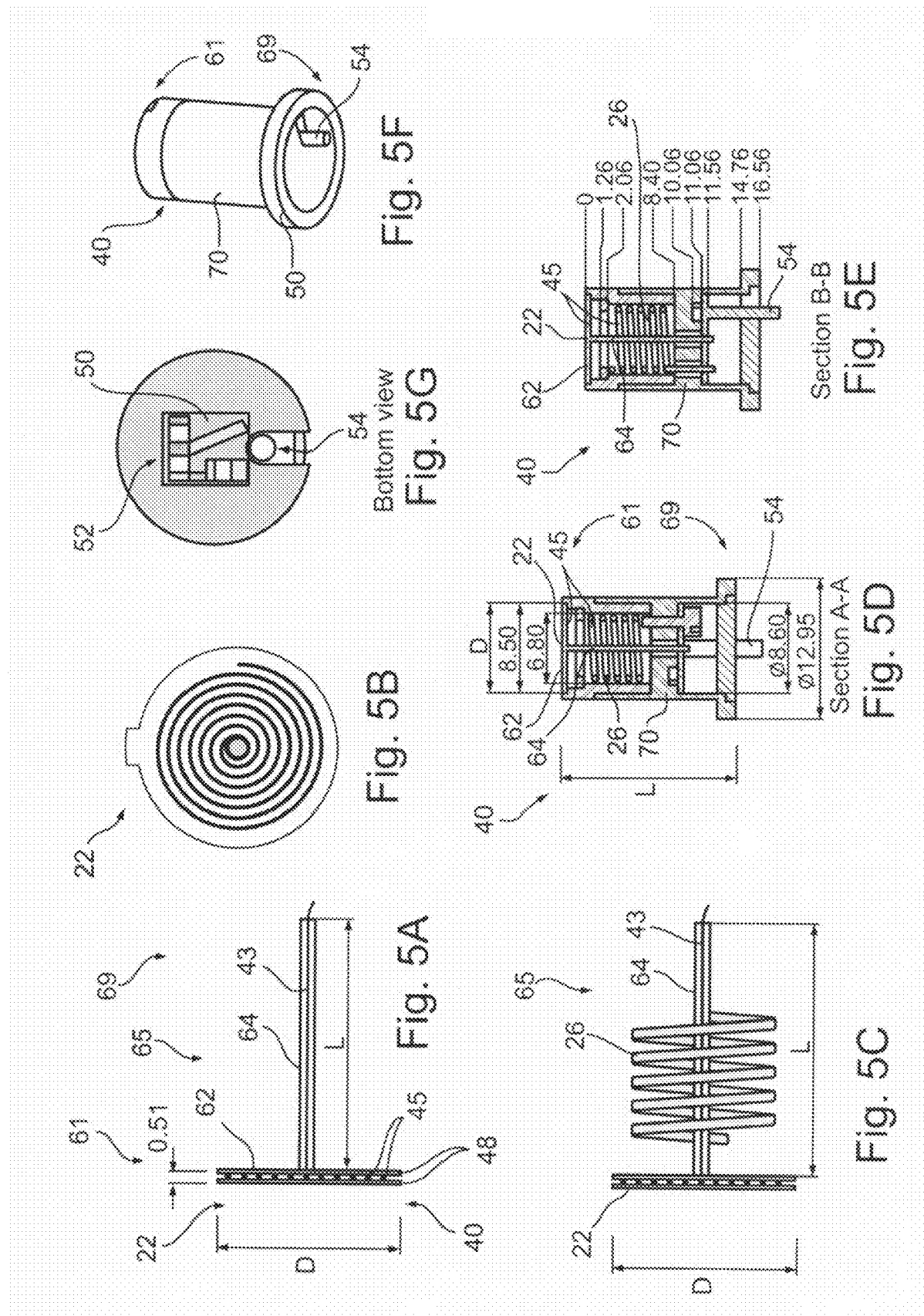

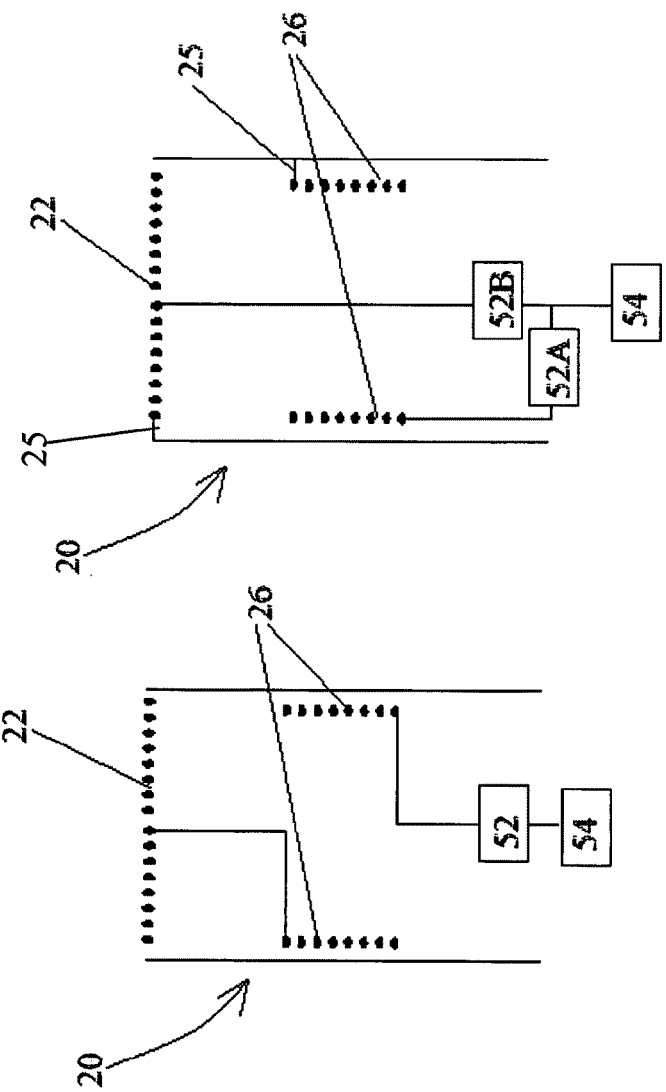
Figure 6C
Figure 6B
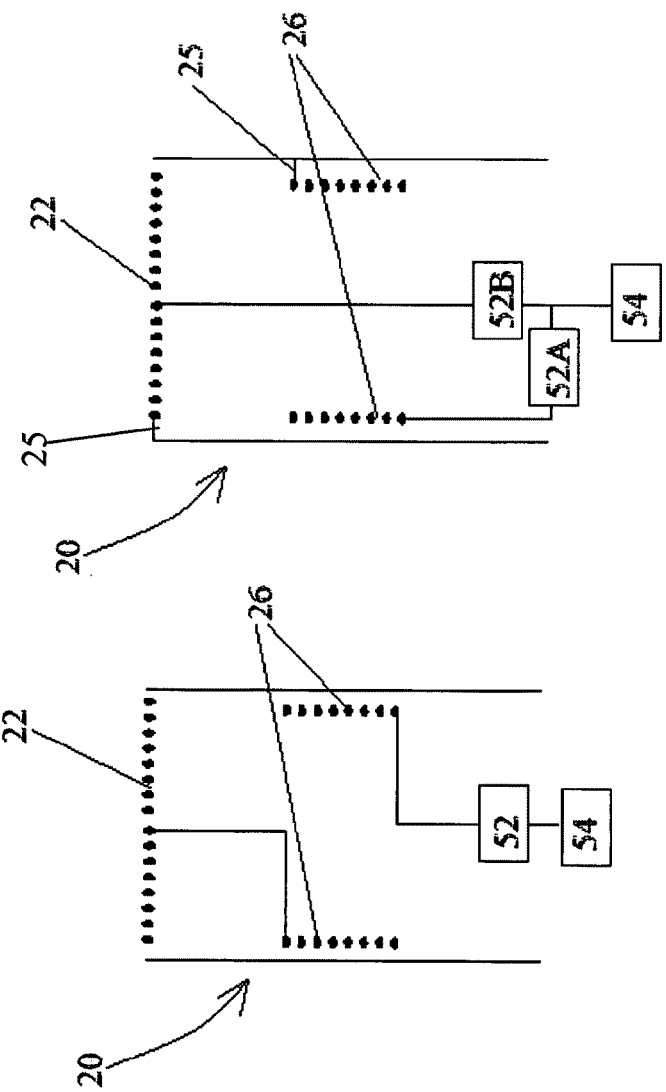
Figure 6A

ELECTROMAGNETIC SENSORS FOR TISSUE CHARACTERIZATION

RELATED APPLICATIONS

This application is a National Phase of PCT Patent Application No. PCT/IL2006/000392 having International Filing Date of Mar. 29, 2006, which claims the benefit of U.S. Provisional Patent Application No. 60/665,842 filed on Mar. 29, 2005. The contents of the above Applications are all incorporated herein by reference.

FIELD OF THE INVENTION

The present invention relates to a method and apparatus for tissue characterization, by resonance of reflected electromagnetic wave signals.

BACKGROUND OF THE INVENTION

Tissue characterization by its electromagnetic reflective properties, for differentiating between tissue types, is known. In general it involves the propagation of an electromagnetic wave at about the microwave range, in a coaxial cable, from an electromagnetic-wave generator to the tissue to be characterized. At the proximal end with respect to the tissue, the coaxial cable may be cut and brought in contact with the tissue. Alternatively, various geometries may be provided, as coaxial endings, operative as a tissue probes.

For example Burdette, et al. [Burdette et al, "In Vivo Probe Measurement Technique for Determining Dielectric Properties at VFW Through Microwave Frequencies", IEEE Trans. On Microwave Theory & Techniques, MTT-28 (4): 414-427, 1980] describe theoretically and experimentally the use of a probe technique in order to determine the dielectric properties of semisolid material and living tissue, in situ. This method is advantageous compared to previous methods known by the following:

1. enabling measurements of the dielectric properties in living tissue in a continuous frequency range of between about 0.1 GHz and about 10 GHz, 2. eliminating the need for tedious sample preparation, and 3. enabling data processing on a real-time basis.

The Burdette idea is to use a short monopole antenna, suitable for insertion into living tissues, as the in vivo probe. The probe is designed as a coaxial cable having an outer and an inner (center) conductor separated by a Teflon dielectric material. The inner conductor cable is slightly longer than the outer one in order to create an electric field of a monopole at the distal tip with respect to operator. This tip is to be inserted into the tissue, which dielectric properties are to be measured. The outer conductor may be grounded for minimizing fringe effects. An SMA connector is attached to the probe by first removing the inner conductor and the Teflon dielectric material, soldering it to the outer conductor and then reassembling the probe with the center conductor as the center pin of the connector. While disassembled, the probe conductors are flashed with nickel plating and then plated with gold in order to reduce chemical reactions between the probe and the electrolyte within the tissue to be examined. This process virtually eliminates oxidation of the probes metallic surfaces and helps minimize electrode polarization effects at lower frequencies.

U.S. Pat. No. 5,744,971, to Chan et al., teaches the use of a coaxial probe for measuring the dielectric properties of materials suitable, although not exclusively so, for the use in the non-invasive monitoring of the conservation treatment of cultural material e.g. works of art such as canvas. The probe is a needle like device with the coaxial structure extending to the distal tip with respect to the operator. The probe is extracorporeal as opposed to the invasive probe of Burdette. The design of this coaxial probe differs slightly from the one of Burdette et al.

U.S. Pat. No. 6,026,323, to Skladnev et al. describes a probe to characterize tissue types that combines optical and electrical tests in a single device, capable of providing the optical and electrical data almost simultaneously from very small areas of a tissue surface. Key to this approach is an instrument capable of making almost simultaneous electrical and optical measurements on the same small areas of tissue. Each measurement involves a complex sequence of events which includes: optical and electrical tissue stimulations with subsequent detection, filtering and digitization of the tissue response; extraction of specific parameters from the optical and electrical signals; checking for errors, and subsequent classification of the extracted parameters into various tissue type categories; and feedback to the system operator. The probe has a central optical fiber, which conducts electromagnetic radiation to a photo-detector diode in the handle and is positioned in the center of a bundle of optical fibers all of which are located within an external tube. A three gold electrodes are positioned adjacent and abutting against the internal surface of the external tube. The probe cable consists of many individual coaxial conductors with a single overall braided shield, enclosed in a medically rated silicone outer jacket. Both ends of the cable have round plastic pin male connectors. The electrodes and optical fibers come into direct contact with the tissue for stimulation and detection of the tissue characteristics. The probe tip is polished and smoothed and has contoured edges. An epoxy resin electrically insulates and seals the tip section.

Commonly owned U.S. Pat. No. 6,813,515 to Hashimshony teaches a probe, method and system for examining tissue, in order to differentiate it from other tissue, according to its dielectric properties. The method is of generating an electrical fringe field in the examined tissue to produce a reflected pulse therefrom with negligible radiation penetrating into the tissue itself; detecting the reflected electrical pulse; and comparing electrical characteristics of the reflected electrical pulse with respect to the applied electrical pulse to provide an indication of the dielectric properties of the examined tissue. The measuring device is built as a coaxial probe with cavity at its distal tip with respect to operator where a sample of the tissue to be examined is confined. The probe itself has an inner conductor insulated from, and enclosed by, an outer conductor open at one end and extending past the inner conductor in the axial direction, defining an open cavity at the distal end of the probe with respect to the operator. The inner conductor includes a tip within the open cavity, which tip is formed with at least two different diameters for enhancing the electrical fringe field.

U.S. Pat. No. 6,370,426, to Campbel et al., describes a method and apparatus for measuring relative hydration of a substrate. Measurements of the electrical characteristics of the substrate, the force applied to it, and the temperature of the substrate during the measurement provide inputs for determining such relative hydration of the substrate. The structure of the sensor used in this case is of two coaxial conductors one of which runs along the axis of symmetry, separated by a coaxial insulator and having a coaxial insulator outside the outer conductor. Both conductors and the separating insulator end at a plane perpendicular to the axis of symmetry at the distal tip with respect to the operator, so that the coaxial structure comes to contact with the examined tissue but does not penetrate it.

British Patent GB01153980, to Einat et al., describes an RF antenna, operative as a probe for near field identification and characterization. It has first and second radiative portions, generating electromagnetic fields, which are substantially opposing, so as to suppress far field radiation. The far-field suppression minimizes contribution from the far field, when near field characterization is sought.

U.S. Pat. No. 6,380,747, to Goldfine, et al., describes a method for processing, optimization, calibration, and display of measured dielectrometry signals. A property estimator is coupled by way of instrumentation to an electrode structure and translates sensed electromagnetic responses into estimates of one or more preselected properties or dimensions of the material, such as dielectric permittivity and ohmic conductivity, layer thickness, or other physical properties that affect dielectric properties, or presence of other lossy dielectric or metallic objects. A dielectrometry sensor is disclosed which can be connected in various ways to have different effective penetration depths of electric fields but with all configurations having the same air-gap, fluid gap, or shim lift-off height, thereby greatly improving the performance of the property estimators by decreasing the number of unknowns. The sensor geometry consists of a periodic structure with, at any one time, a single sensing element that provides for multiple wavelength within the same sensor footprint.

The systems described hereinabove are non-resonating, so the differences between signals from different tissue types are small.

By contrast, U.S. Pat. No. 5,227,730, to King, et al., U.S. Pat. No. 5,334,941, to King, and U.S. Pat. No. 6,411,103, to Tobias add an element of resonance.

U.S. Pat. No. 5,227,730, to King, et al. teaches a method and apparatus for sensing complex dielectric properties of lossy (dissipative) dielectric materials in vivo or in vitro, particularly biological tissue. This idea is based on a needle-like resonant sensor, which is inserted into the test material for measuring its dielectric properties at the resonant frequency. The major advantage, compared to the sensors described hereinabove, is that due to the resonating effect, the dielectric constants can be measured with a greater accuracy and resolution, and over a much larger volume (of the order of a cubic centimeter). Thus, the resonant sensor is able to better distinguish between tumors and normal tissue. The needle-like resonant sensor, as designed by King, et al., has the form of a dipole resonator that is positioned parallel and adjacent to a miniature coaxial feed cable and is electrically insulated from it. The dipole resonator is inductively coupled to the microwave power in the coaxial cable by means of an electrically short circumferential gap cut in the cable shield. By coupling the gap to the dipole at its center currents are induced in the dipole in a perfectly balanced and symmetric manner. With proper design of the feed gap, the dipole impedance can be well matched to the coaxial cable with very small reflection from the gap at the resonant frequency of the dipole. To regulate the degree of coupling between the dipole and the test medium, a thin cylindrical dielectric sheath encloses the entire assembly. Such a sheath might be, for example, a dielectric catheter into which the coaxial cable with its attached dipole resonator is inserted.

U.S. Pat. No. 5,334,941, to King, describes a highly sensitive, direct-contact, in situ sensor for nondestructively measuring or monitoring the complex dielectric and conductive properties of solids, liquids, or gasses at microwave frequencies. A metal microstrip dipole resonator is etched on the surface of a dielectric substrate which is bonded to a copper ground plane. The dipole resonator is electromagnetically driven by mutual inductive coupling to a short nonresonant feed slot formed in the ground plane. The slot is driven by a coaxial feed line or a microstrip feed line extending from a swept microwave frequency source which excites the incident wave. Alternatively, the metal resonator is omitted and the length of the slot is increased so that it becomes the resonator. In use, the sensor is placed in close physical contact with the test material having complex dielectric constant .epsilon.* (=.epsilon.'-j.epsilon.") or conductivity .sigma. As the frequency of the microwave source is swept, a sharp dip in the reflected wave occurs at the resonant frequency, provided that the coaxial feed line or microstrip feed line is nearly critically coupled to the sensor input. Measurement of the resonant frequency and input coupling factor determines small changes in .epsilon.', .epsilon." and .sigma. with great resolution. To diminish the electromagnetic coupling between the resonator and the test material, and to protect the resonator from damage and wear, a superstrate may be added.

U.S. Pat. No. 6,411,103, to Tobias, et al., describes a stray-field sensor for measuring dielectric properties of substances includes generating elements for generating an electrical field and shielding elements for shielding the generated electrical field. The shielding elements have at least two openings for coupling the electrical field out into the outside space so that the electrical field is at least partially located outside of the shielding elements.

Additionally, German applications DE 19705260A1 DE 19734978A1 describe systems in which the substances to be examined are brought into the resonator, to influence the resonant frequency of the resonant circuit.

SUMMARY OF THE INVENTION

The present invention relates to a sensor for tissue characterization, comprising: a resonator, configured to be placed proximally to an edge of a tissue for characterization, without penetrating the tissue, the resonator comprising a conductive structure associated with a diameter-equivalent dimension D, in a plane substantially parallel with the edge, and with a feature size d; and at least one conductive lead, for providing communication with an external system, wherein the resonator is configured to resonate at a frequency which corresponds to a free-air wavelength range of between about $\lambda$ and about $40\lambda$, wherein $\lambda$ is at least about ten times the diameter-equivalent D, and wherein upon receiving a signal in the range of between about $\lambda$ and about $40\lambda$, the sensor is configured to induce electric and magnetic fields, in a near zone, in the tissue, the near zone having a diameter of about D, so that the tissue in the near zone effectively functions as part of the resonator, influencing its resonating values, and so the tissue in the near zone is thereby characterized by its electromagnetic properties, by the resonating response of the resonator.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
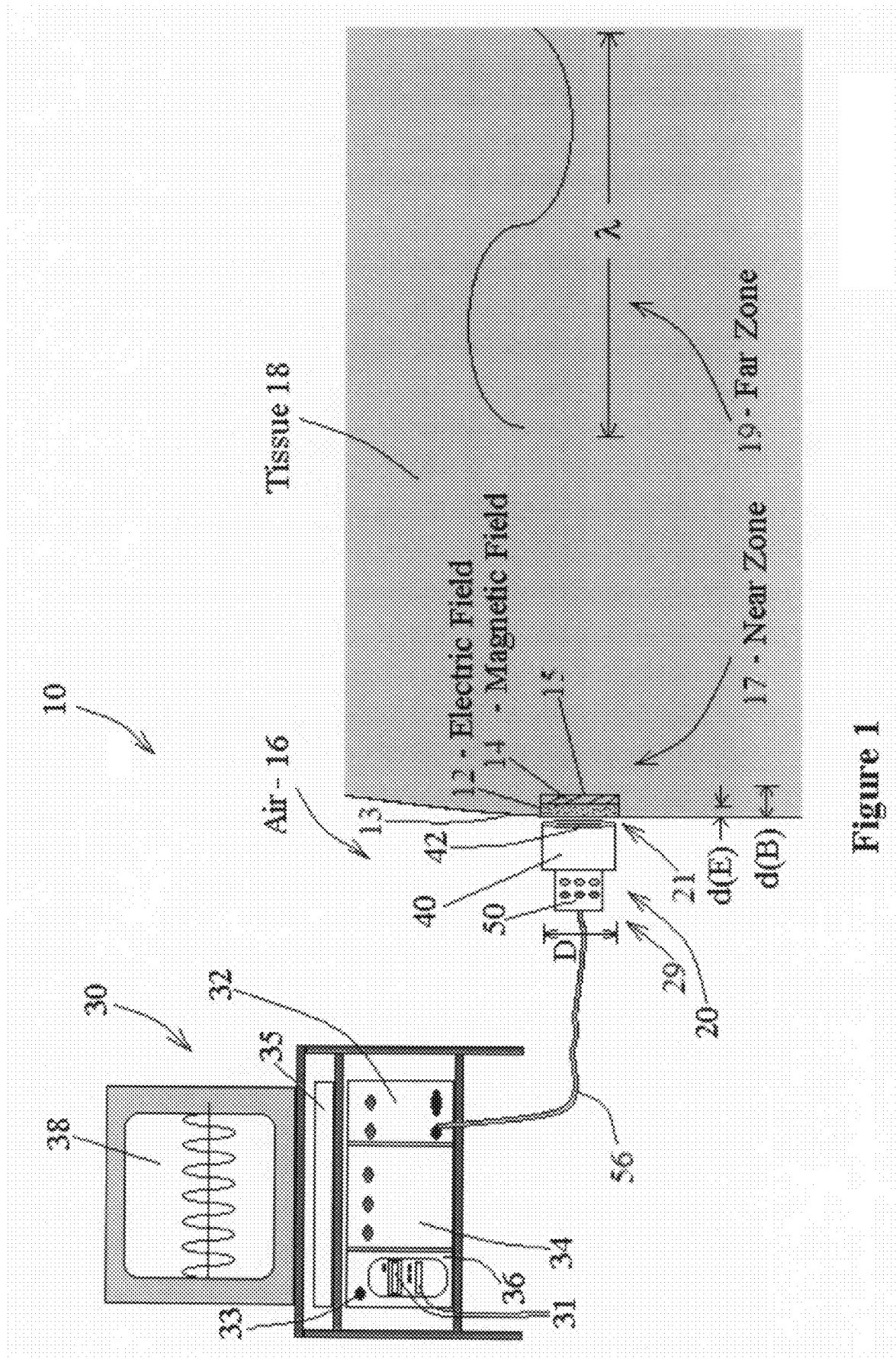
Figure 2A:
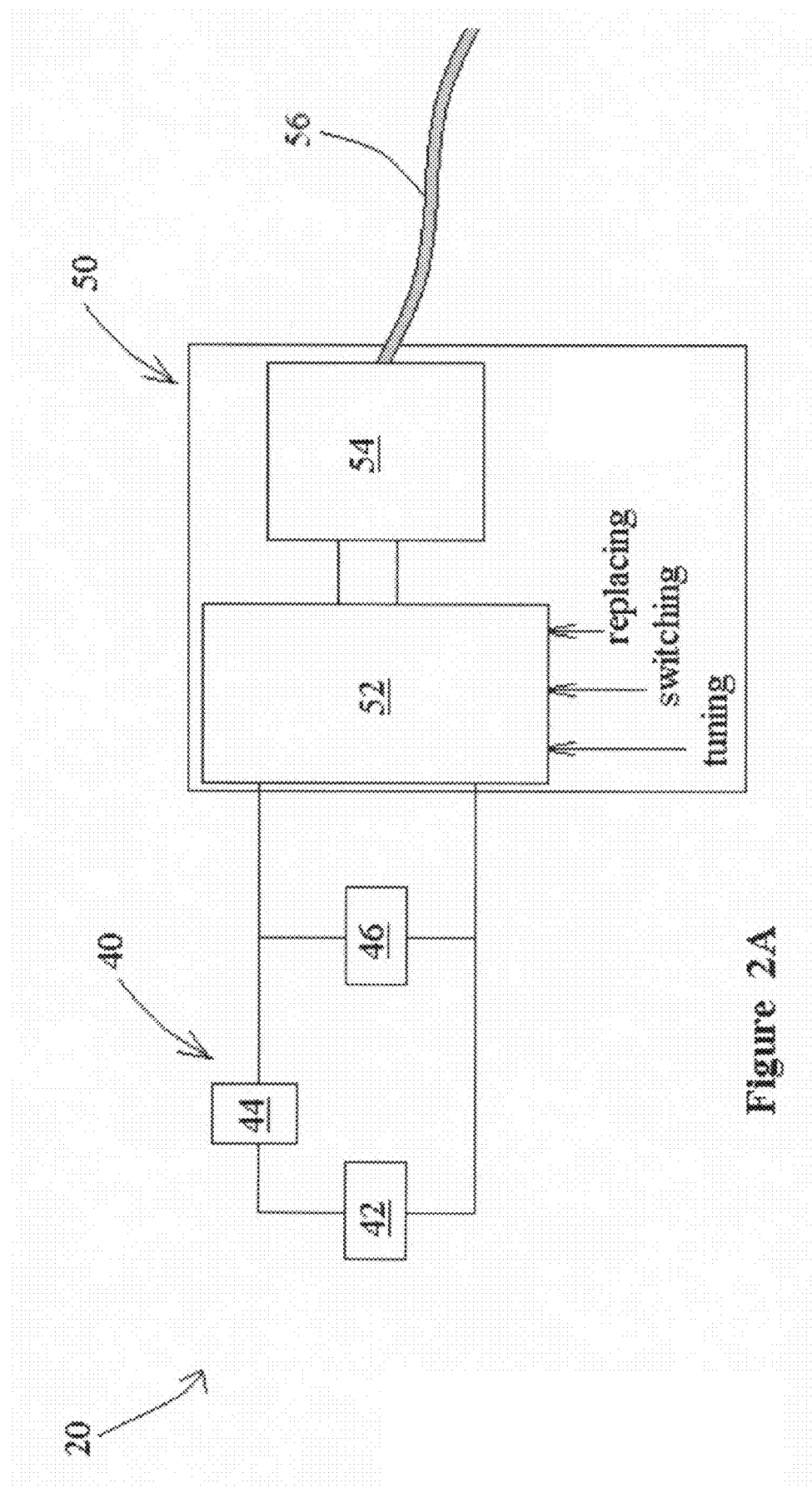
Figure 2B:
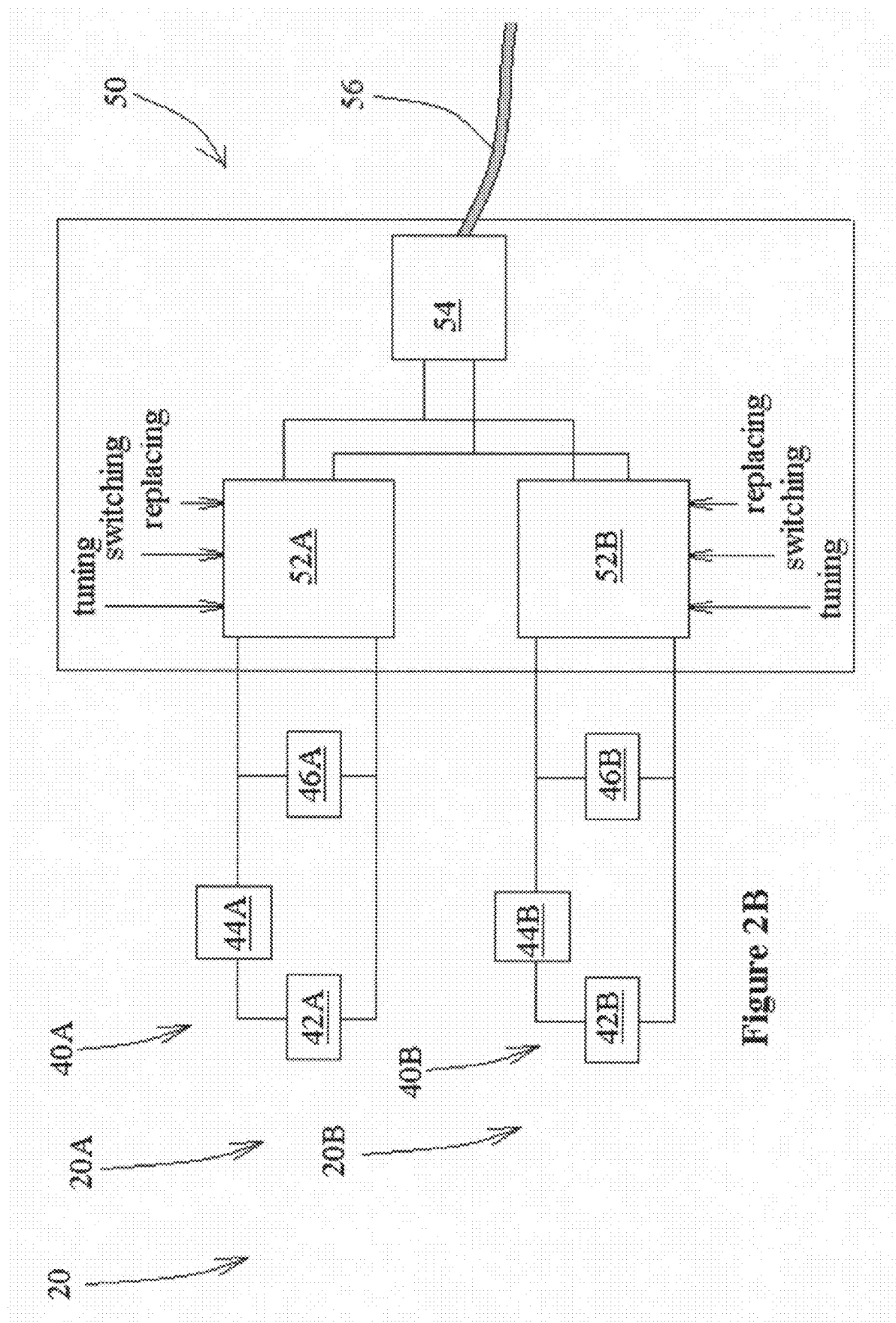
Figure 3D:
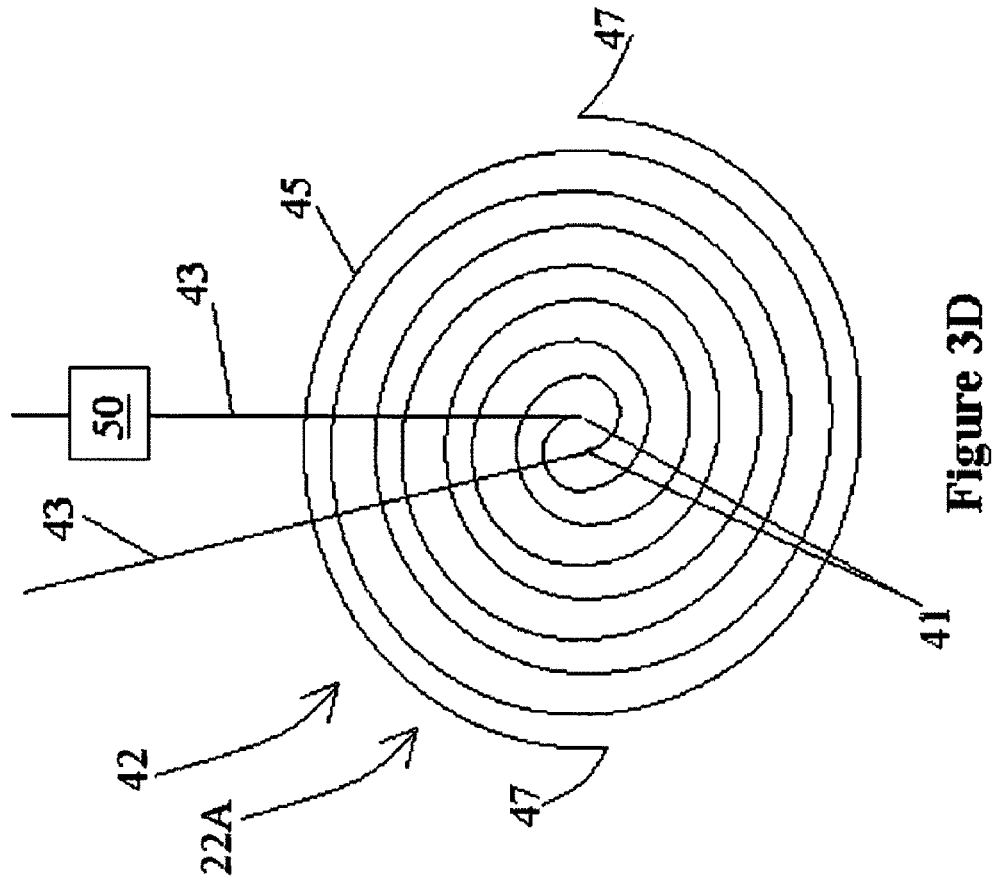
Figure 3C:
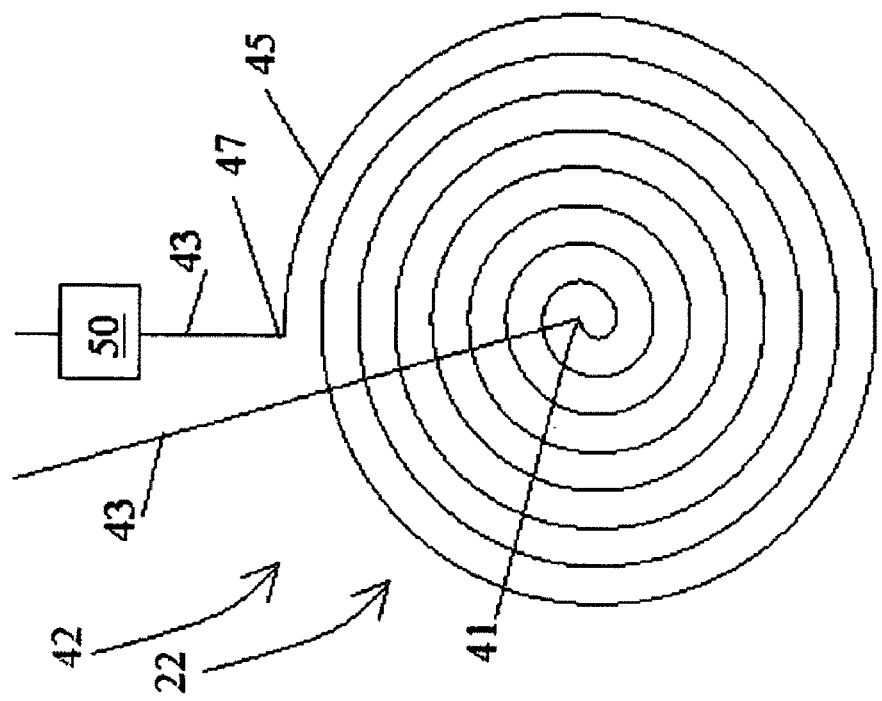
Figure 3E:
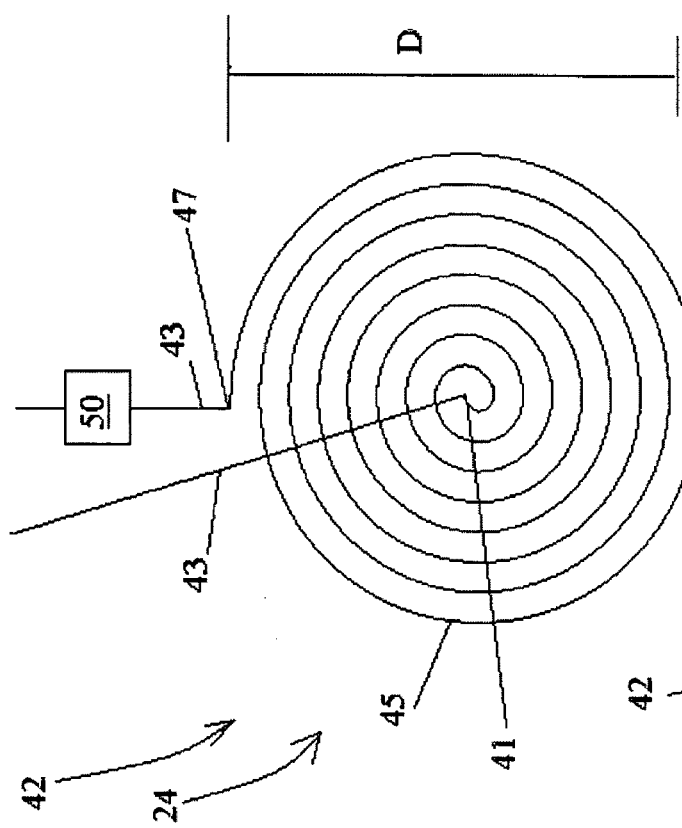
Figure 3F:
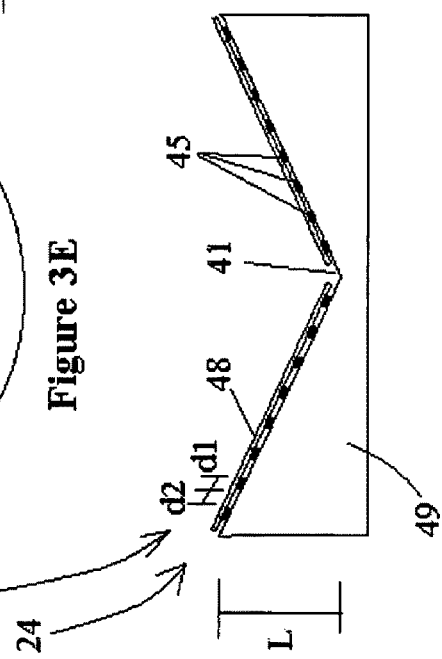
Figure 3N:
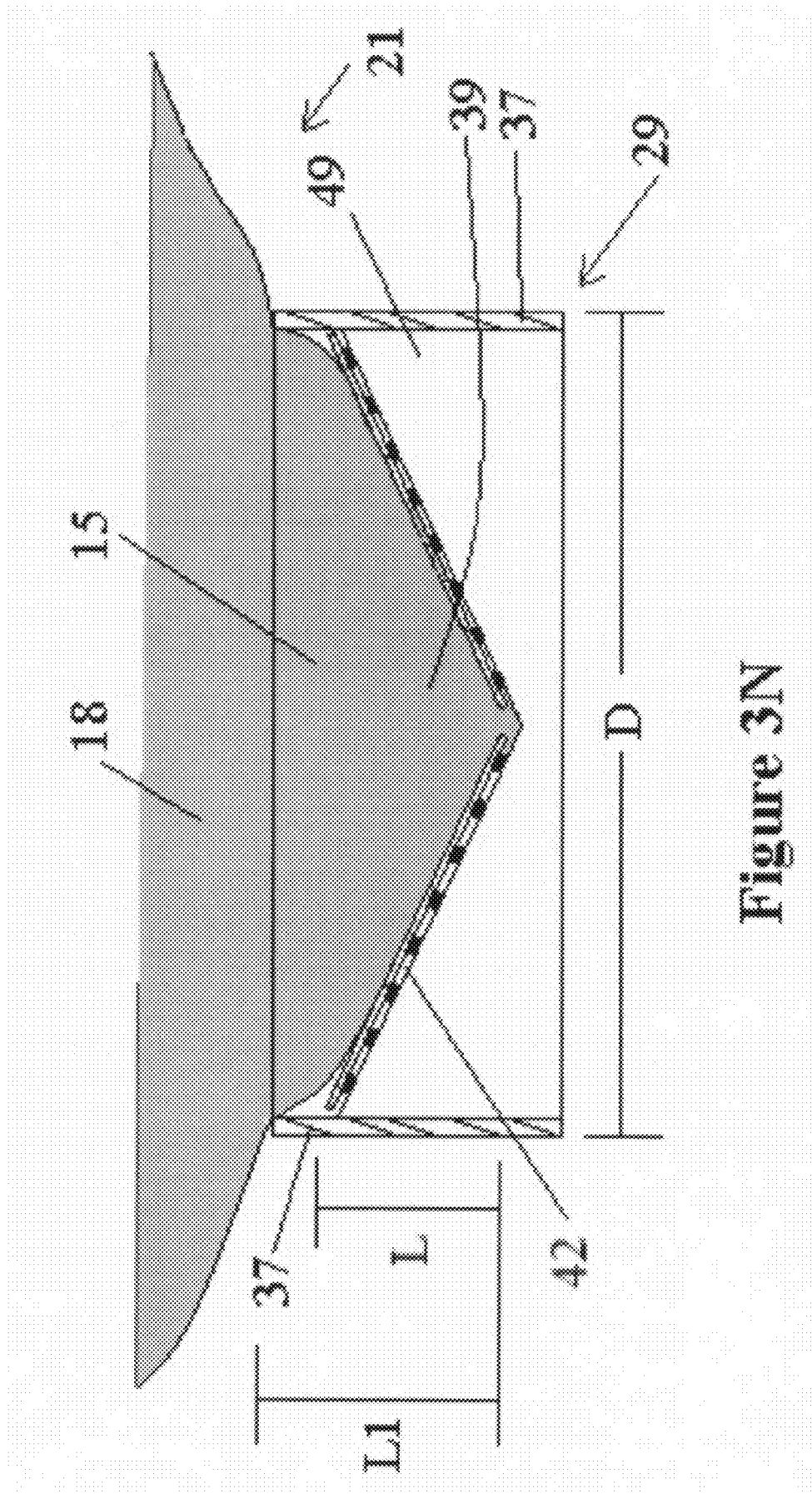
Figure 4A:
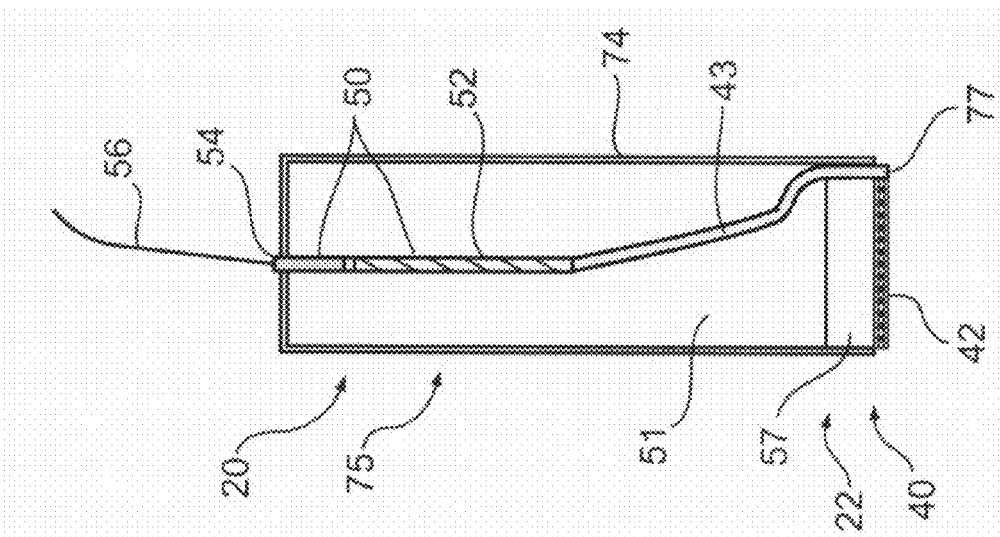
Figure 4B:
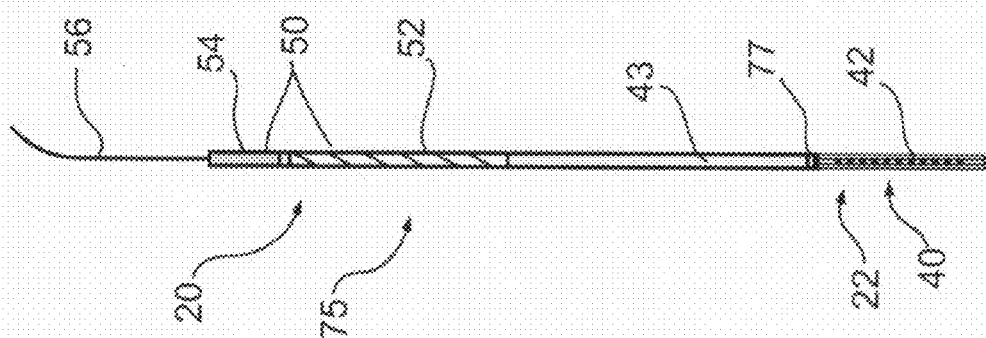
Figure 4C:
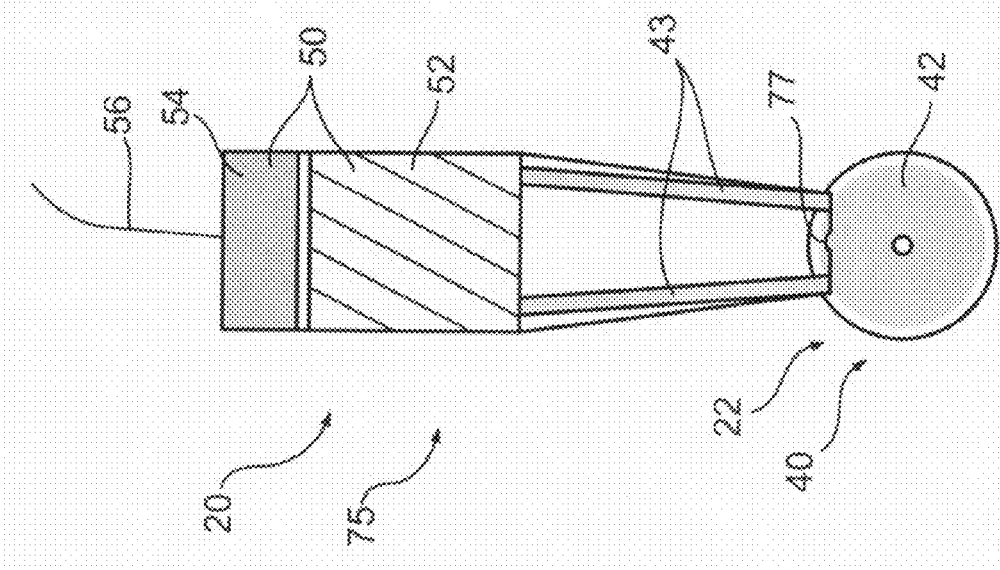
Figure 7A:
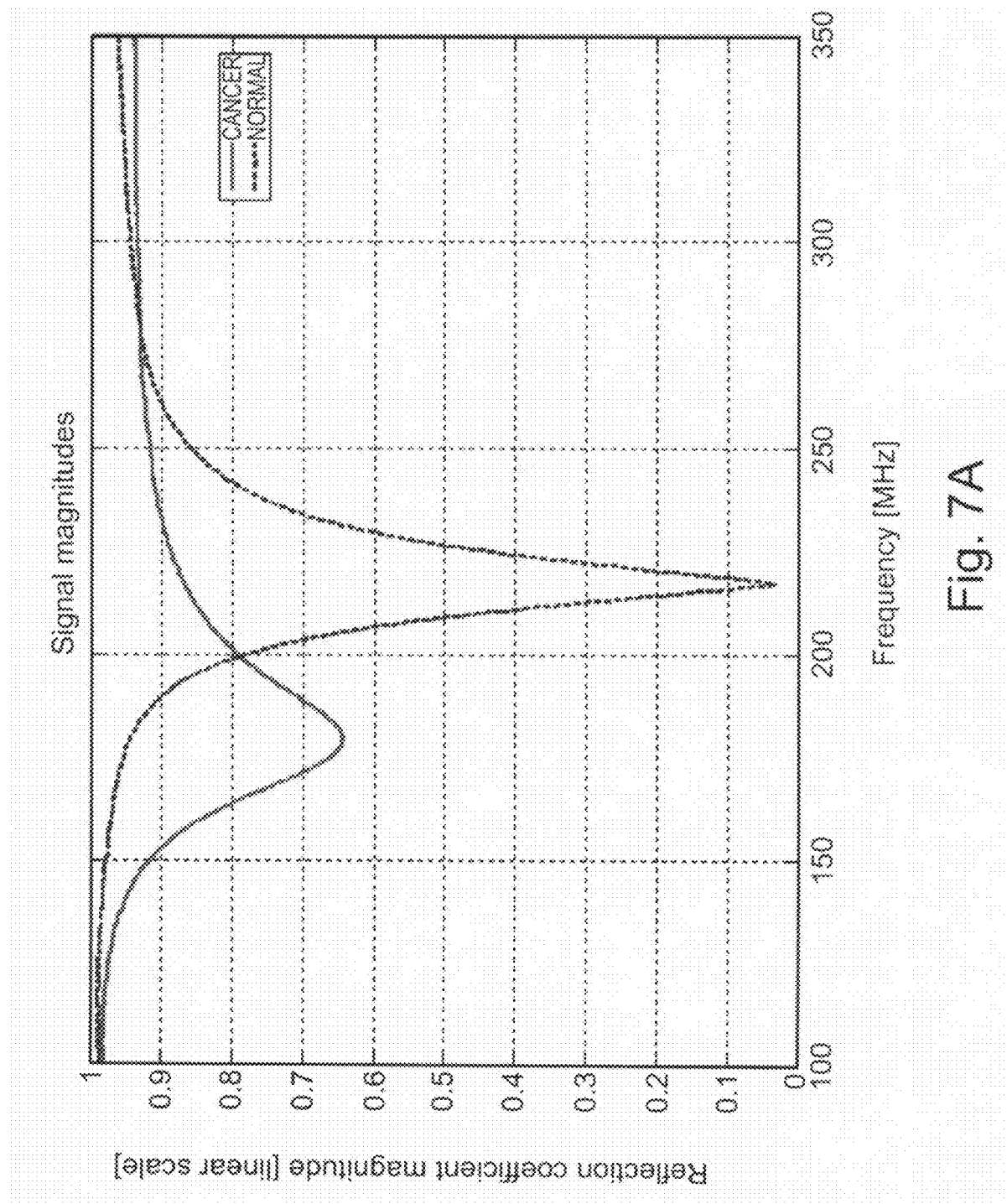
Figure 7B:
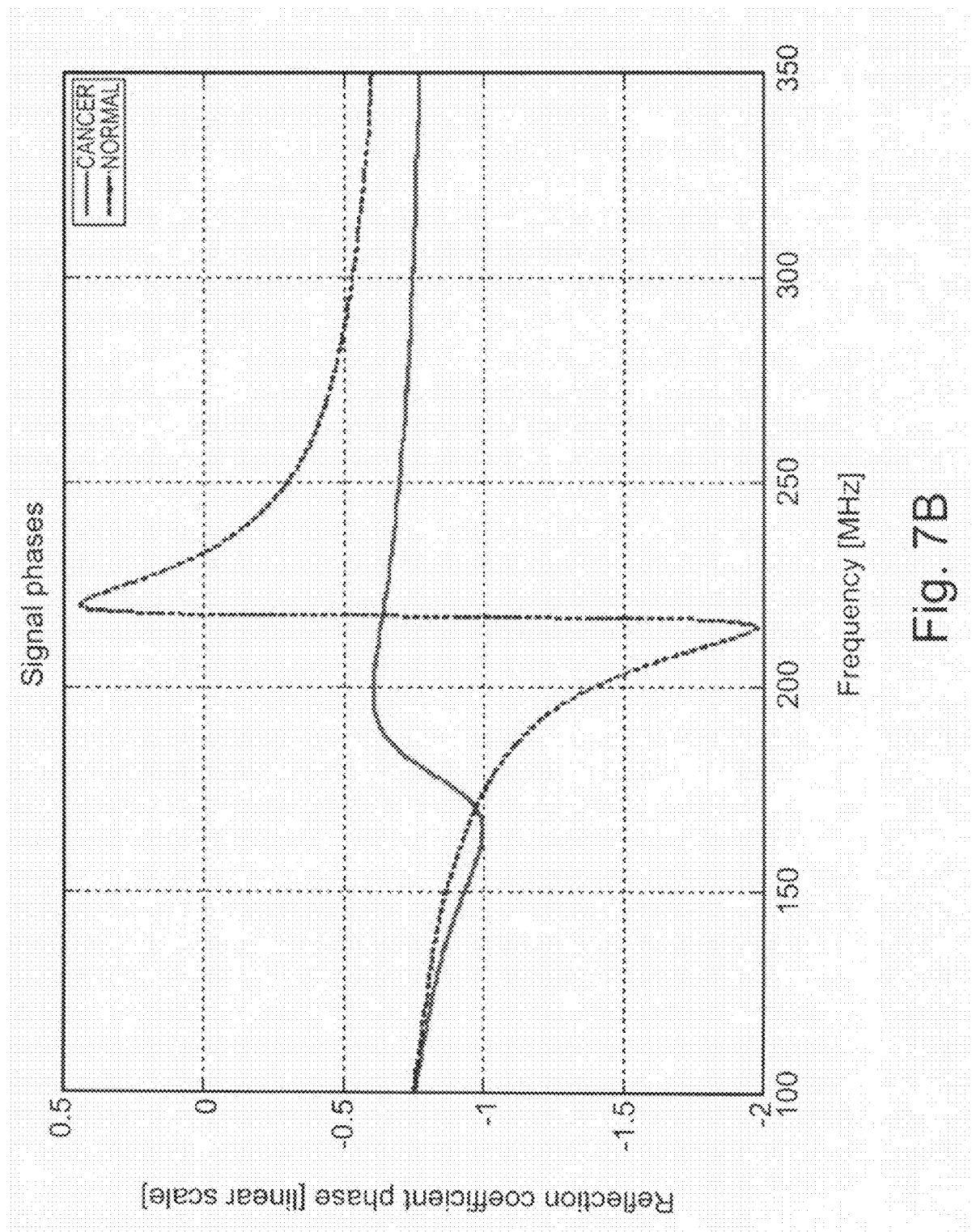

FIG. 1 schematically illustrates a system and a sensor for tissue characterization, in accordance with some embodiments of the present invention;

FIGS. 2A-2B schematically illustrate schematic circuits for the sensor for tissue characterization, in accordance with some embodiments of the present invention;

FIGS. 3A-3N schematically illustrate various geometries for the conductive structures of the sensor for tissue characterization, in accordance with some embodiments of the present invention;

FIGS. 4A-4C schematically illustrate the sensor for tissue characterization, formed as a thin, flexible construction, in accordance with an embodiment of the present invention;

FIGS. 5A-5G schematically illustrate the sensor for tissue characterization operative with a housing, in accordance with some embodiments of the present invention;

FIGS. 6A-6C schematically illustrate various manners of combining spiral and a helix, in accordance with some embodiments of the present invention; and FIGS. 7A and 7B schematically illustrate experimental data of the sensor for tissue characterization of the present invention.

DESCRIPTION OF THE PREFERRED EMBODIMENTS

The present invention relates to a sensor for tissue characterization, comprising: a resonator, configured to be placed proximally to an edge of a tissue for characterization, without penetrating the tissue, the resonator comprising a conductive structure associated with a diameter-equivalent dimension D, in a plane substantially parallel with the edge, and with a feature size d; and at least one conductive lead, for providing communication with an external system, wherein the resonator is configured to resonate at a frequency which corresponds to a free-air wavelength range of between about λ and about 40λ, wherein λ is at least about ten times the diameter-equivalent D, and wherein upon receiving a signal in the range of between about λ and about 40λ, the sensor is configured to induce electric and magnetic fields, in a near zone, in the tissue, the near zone having a diameter of about D, so that the tissue in the near zone effectively functions as part of the resonator, influencing its resonating values, and so the tissue in the near zone is thereby characterized by its electromagnetic properties, by the resonating response of the resonator.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 schematically illustrates a system 10, having a sensor 20 for tissue characterization, in accordance with a first embodiment of the present invention.

The sensor 20 has proximal and distal ends, 21 and 29, with respect to a tissue 18, which is the tissue to be characterized.

The sensor 20 includes a conductive structure 42, configured to be placed proximally to an edge 13 of the tissue 18 for characterization, while in air 16, that is, without penetrating the tissue 18.

In accordance with a first embodiment, illustrated in FIG. 1, the conductive structure 42 is operative as a resonating sensor 20.

The conductive structure 42 defines a diameter-equivalent D—the diameter of a circle having a cross sectional area which is substantially the same as the cross-sectional area of the element 42. Thus D defines a cross-sectional area on a side of the edge 13, substantially parallel with the edge 13. Preferably, D is between about 3 mm and 25 mm. It will be appreciated that other values, which are larger or smaller, may similarly be used. The conductive structure 42 further defines a feature size d, which is based, for example, on a wire thickness and wire spacing, as shown hereinbelow, in conjunction with FIG. 3B.

Additionally, the conductive structure 42 is associated with a circuit 40, by resistance coupling or by inductive or capacitance coupling. The circuit 40 communicates with an external signal-generation-control-and-analysis system 30, via a coupler 50 and a transmission line, for example, a coaxial cable 56.

The conductive structure 42 is configured to resonate at a free-air wavelength range of between about λ and about 40λ, wherein λ is at least about ten times the diameter-equivalent D. Thus, the free-air wavelength range of between about λ and about 40λ is generally equivalent to a frequency range of between about 10 Mhz and about 5 Ghz.

Upon receiving a signal in the range of between about λ and about 40λ, the conductive structure 42 is configured to induce an electric field 12 and a magnetic field 14, in a near zone 17 of the tissue 18, wherein the electric field 12 penetrates the tissue 18 to a depth of d(E) and the magnetic field 14 penetrates the tissue 18 to a depth of d(B), both being of the order of magnitude of the feature size d. Preferably, d(B) is somewhat larger than d(E), for example, by a factor of between 1.1 and 5. Alternatively, they are substantially the same. However, it will be appreciated that in some cases, d(B) may be smaller than d(E).

Thus, the region of penetration is generally a disk 15 of a diameter, which is about the diameter-equivalent D, and a thickness of about the feature size d, which begins with the tissue edge 13. The tissue 18 in the disk 15 effectively functions as part of the resonator, varying its resonating response. In consequence, the tissue 18 in the disk 15 may be characterized based on its electromagnetic properties, by its resonating response.

Additionally, the conductive structure 42 is configured as an inefficient antenna, for the free-air wavelength range of between about λ and about 40λ, so its radiation efficiency in a far zone 19 is less than 0.1%, and preferably less than 0.01%. As a result, contributions of the far zone are minimized and the tissue characterization is limited to the disk 15 of the near zone 17, very close to the edge 13.

The effect is similar to that achieved by British Patent GB01153980, to Einat et al., which describes an RF antenna, operative as a probe for near field identification and characterization. It has first and second radiative portions, generating electromagnetic fields, which are substantially opposing, so as to suppress far field radiation. The far-field suppression minimizes contribution from the far field, when near field characterization is sought.

The external signal-generation-control-and-analysis system 30 preferably includes a signal generator 32, an analyzer 34, and a controller 36, although these may be integrated into a single unit. A user interface may be provided, for example, in the form of read and write drives 31, such as, a diskette, a CD, a DVD, a disk-on-key and the like, for providing predetermined operating parameters and settings, and in order to store test results. A display screen 38 may display the resonating response. It will be appreciated that other output means, for example, a printer or a facsimile, are also possible. A keyboard 35 may be used to input data such as patient details, date and time of a particular test, signal parameters, and the like. Additionally, the controller 36 may include other input and output devices, for example, a USB port 33, and other features, as known.

Referring further to the drawings, FIGS. 2A and 2B illustrate schematic circuits of the sensor 20, in accordance with other embodiments of the present invention, wherein the conductive structure 42 together with an electronic support structure is operative as the resonating sensor 20.

As seen in FIG. 2A, the sensor 20 may be represented as a circuit 40, which includes the conductive structure 42, configured to be placed proximally to the tissue 18. Additionally, the circuit 40 may include an effective component 44, having an effective resistance, an effective inductance, and an effective capacitance, and which may be connected in series with the conductive structure 42, and an effective component 46, having an effective resistance, an effective inductance, and an effective capacitance, and which may be connected in parallel with the conductive structure 42.

Accordingly, either the effective component 44 or the effective components 44 and 46 may form the electronic support structure. Thus the resonating sensor 20 may be effectively formed either of the conductive structure 42 and the effective component 44, or the conductive structure 42 and both the effective components 44 and 46. Thus, in accordance with the present embodiment, it is the overall sensor 20 which is configured to resonate at a frequency which corresponds to a free-air wavelength range of between about λ and about 40λ.

The coupler 50 preferably includes a connection structure 52, which preferably provides at least one of tuning, switching, and replacing capabilities, for example, in order to change the overall impedance of the circuit 40, or of the components 44 and 46. These capabilities may be desired to interchangeably optimize the sensor 20 for characterizing different types of tissue, for example, breast tissue, which is predominantly fat, muscle tissue, skin tissue, and bone.

A connector 54 connects the connection structure 52 and the transmission line 56, preferably, while ensuring impedance matching and balancing.

As seen in FIG. 2B, the sensor 20 may be represented as two circuits 40A and 40B, forming two resonators, 20A and 20B, and including two conductive structures 42A and 42B, connected in parallel. Additionally, the circuits 40A and 40B may include effective components 44A and 44B, each having an effective resistance, an effective inductance, and an effective capacitance, and which may be connected in series with the conductive structures 42A and 42B, and effective components 46A and 46B, each having an effective resistance, an effective inductance, and an effective capacitance, and which may be connected in parallel with the conductive structures 42A and 42B.

The resonator 20A may be effectively formed of the conductive structure 42A and the effective component 44A, or the conductive structure 42A and both the effective components 44A and 46A. The resonating sensor 20B may be effectively formed of the conductive structure 42B and the effective component 44B, or the conductive structure 42B and both the effective components 44B and 46B Additionally, the two circuits 40A and 40B may be associated with connection structures 52A and 52B, which preferably provide at least one of tuning, switching, and replacing capabilities to the circuits 42A and 42B.

The connector 54 connects the connection structures 52A and 52B and the transmission line 56, preferably, while ensuring impedance matching and balancing.

Referring further to the drawings, FIGS. 3A-3N schematically illustrate various geometries for the conductive structure 42 of the sensor 20 for tissue characterization, in accordance with some embodiments of the present invention, As seen in FIGS. 3A and 3B, the conductive structure 42 is formed as a flat spiral 22, of a conductive material, such as copper, gold, or another conductor, as known. An inner end 41 may be resistively connected to the coupler 50, via a conductive lead 43. However, a second end 47 may be free, so as to be inductively or capacitively coupled to the circuit 40 (FIG. 2A). Alternatively, the second end 47 may be connected to the coupler 50, while the first end 41 may be free.

The spiral 22 is associated with the diameter-equivalent D.

As seen in FIG. 3B, the spiral 22 may be deposited on a substrate 49, to a thickness of about 2-30 microns. It will be appreciated that other dimensions may similarly be used. The substrate may be, for example, polycarbon, quartz, or another material as known. The purpose of the substrate 49 is to provide a mechanical support to the sensor 20.

Preferably, an insulation layer 48, for example, Kapton, of about 4-50 microns, may be applied over the spiral 22. It will be appreciated that other dimensions may similarly be used.

The width d1 of the conductive material 45, and the spacing d2 are generally of the same order of magnitude, and are termed, the feature size, denoted here generally as d. The feature size d may influence the resolution capability of the sensor 20, especially the spatial resolution and is preferably no more than half the size of the desired resolution capability. For example, when a minimal detectable object size of about 0.25 mm is sought, a feature size which is about of about 0.1 mm, being 40% of the desired resolution capability may be used.

Preferably, the feature size d is between about 1/10 and 1/20 of the diameter-equivalent D.

FIG. 3C illustrates the spiral 22, with both ends 41 and 47 resistively coupled to the circuit 40, via conductive leads 43.

FIG. 3D illustrates a double spiral 22A, with the two inner ends 41 resistively coupled and the two outer ends 47, being free.

FIGS. 3E and 3F schematically illustrate a conical helix 24, which is similarly deposited on the substrate 49. However, the substrate 49 is shaped as a funnel, to provide the conductive material 45 with the cone shape.

The conical helix 24 is associated with the diameter-equivalent D and with a length L. Additionally, it is associated with the width d1 of the conductive material 45, and the spacing d2, as for the spiral 22. The conical helix 24 is shown resistively coupled. Alternatively, it may be inductively or capacitively coupled.

FIGS. 3G-3K schematically illustrate the conductive structure 42, wherein the conductive material 45 is formed as two combs 45A and 45B, inserted into each other, as shown in FIGS. 3H and 3I, to form a structure 28.

The conductive material 45 forming the structure 28 may be deposited on the insulating material 48, such as Kapton, of a thickness of about 100 microns, and covered with the insulating material 48, such as Kapton of a thickness of between about 4 and 50 microns.

Contact points 55 provide resistive coupling to the structure 28.

Preferably, the structure 28 is placed over a hollow region 51, formed by a housing 53. The purpose of the hollow region 51 being to prevent a response from a distal side of the structure 28. Alternatively, an electrical insulator 51 may be used in place of the hollow region 51.

FIGS. 3L and 3N further illustrate the conical helix 24, of FIG. 3F, deposited on the substrate 49, shaped as the funnel, to provide the conductive material 45 with the cone shape.

A preferably tubular wall 37 of a conductive material encloses the conical helix 24, extending beyond the conical helix on the proximal side 21 with respect to the tissue, so as to form an open cavity 39.

Thus, whereas the conical helix 24 has a length L, the wall 37 has a length L1, which is somewhat larger than L, for example, by 10-100%.

As before, the conical helix 24 is associated with the diameter-equivalent D and feature sizes d1 and d2, of substantially similar in value, so as to be considered d, wherein the feature size d is preferably about a tenth of the diameter-equivalent D. The conical helix 24 is shown resistively coupled. Alternatively, it may be inductively or capacitively coupled.

In essence, the open cavity 39 is as taught in commonly owned U.S. Pat. No. 6,813,515 to Hashimshony, which describes a method and system for examining tissue by: applying an electrical pulse to the tissue to be examined via a probe formed with an open cavity such that the probe generates an electrical fringe field in the examined tissue within the open cavity and produces a reflected electrical pulse therefrom with negligible radiation penetrating into other tissues or biological bodies near the examined tissue; detecting the reflected electrical pulse; and comparing electrical characteristics of the reflected electrical pulse with respect to the applied electrical pulse to provide an indication of the dielectric properties of the examined tissue.

In the present example, seen in FIG. 3N, the region of penetration of the tissue 18 is contained within the cavity 39. The tissue 18 contained within the cavity 39 effectively functions as part of the resonator, varying its resonating response. In consequence, the tissue 18 contained within the cavity 39 may be characterized based on its electromagnetic properties, by its resonating response.

While the example of FIG. 3N illustrates a conical open cavity, a cylindrical open cavity, for example, formed by adding the conductive tubular walls 37 to the embodiment of FIGS. 3A and 3B, is similarly possible.

It will be appreciated that the conductive structure 42 of any one of FIGS. 3A-3N may also be associated with the circuit 40 of FIG. 2A, by resistance coupling or by inductive or capacitive coupling, wherein the circuit 40 communicates with the external signal-generation-control-and-analysis system 30, via the coupler 50 and the transmission line, for example, the coaxial cable 56.

Alternatively, the conductive structure 42 of any one of FIGS. 3A-3N may also be associated with the circuits 40A and 40B of FIG. 2B, by resistance coupling or by inductive or capacitive coupling.

Referring further to the drawings, FIGS. 4A-4C schematically illustrate the sensor 20, formed as a thin, flexible construction 75, in accordance with an embodiment of the present invention.

Preferably, the sensor 20 includes the spiral 22, of a thickness of about 2-30 microns, deposited on the insulating material 48, such as Kapton, of a thickness of about 100 microns, and covered with the insulating material 48, such as Kapton of a thickness of about 4-50 microns, thus being essentially self-supporting.

The flexible construction 75 is configured to bend at a line 77, so that in operation, the spiral 22 is substantially at a right angle to the remainder of the flexible construction 75. Additionally, the flexible construction 75 is adapted for operation when inserted into a hollow housing 74, having a top cover 57 of polycarbon, wherein the spiral 22 forms a proximal cover over the top cover 57 of polycarbon, for forming contact or near contact with the edge 13 of the tissue 18 (FIG. 1). The hollow housing 74 essentially provides the effective hollow region 51, at the distal side of the sensor 22.

It will be appreciated that the housing 74 may be filled with an insulating material.

It will be appreciated that the flexible construction 75 may be attached to the housing 74 rather than inserted therein.

Referring further to the drawings, FIGS. 5A-5G, schematically illustrate the sensor 20 operative with a housing 70, in accordance with some embodiments of the present invention.

In accordance with the present embodiment, the sensor 20 may include the spiral 22 and a helix 26. These may be connected in series, or in parallel, as shown in FIG. 2B. Additionally, either one may be resistively coupled. Alternatively, either one may be inductively or capacitively coupled, so as to have one free end.

The housing 70 preferably includes an inner support structure 65, having a circular head 62 and a leg 64, so as to have a T-shaped cross section, and having proximal and distal ends 61 and 69, with respect to the tissue.

The spiral 22 is preferably positioned at the head 62. The helix 26 may be coiled around the leg 64. The leg 64 may further be used to house the conductive lead 43 of the spiral 22.

FIG. 5G schematically illustrates the coupler 50 having the connection structure 52 and the connector 54, at the distal end 69 of the housing 70.

Referring further to the drawings, FIGS. 6A-6C schematically illustrate various manners of combining the spiral 22 and the helix 26, in accordance with some embodiments of the present invention.

In FIG. 6A, the spiral 22 and the helix 26 are connected in parallel and both are inductively or capacitively coupled.

In FIG. 6B, the spiral 22 and the helix 26 are connected in series, and both are inductively or capacitively coupled. It will be appreciated that a connection in series which is resistively coupled is also possible.

In FIG. 6C, the spiral 22 and the helix 26 are connected in parallel and both are resistively coupled, via contacts 25.

FIGS. 7A and 7B schematically illustrate experimental data of the sensor for tissue characterization of the present invention.

FIG. 7A illustrates a reflection coefficient amplitude of a reflection signal.

FIG. 7B illustrates a reflection coefficient phase of a reflection signal.

It will be appreciated that at least one of the amplitude and the phase may be used. Additionally, both may be used.

FIGS. 7A and 7B illustrate the broadband nature of the resonator of the present invention. Defining a response as a change of at least 10% in the reflection coefficient amplitude of a reflection signal (FIG. 7A), it is noted that the range of the response in FIG. 7A is from about 180 to about 260 MHz. In the present example of FIG. 7A, the range is 80 MHz around a resonating value of 220 MHz.

The broadband is often defined as $\Delta f/f$, or in the present example, 80/220. Expressing the broadband in percentage leads to a value of 36%, or ±18%.

In accordance with other examples of the present invention, the broadband may be as much as ±50%. Alternatively, it may be at least ±25%, or at least ±15%.

It is expected that during the life of this patent many relevant broad-band sensors, for tissue characterization will be developed, and the scope of the term broad-band sensor, for tissue characterization is intended to include all such new technologies a priori.

As used herein, the term "substantially" refers to ±10%.

As used herein, the terms "generally," and "about" refer to ±30%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, any citation or identification of any reference in this application shall not be construed as an admission that such reference is available as prior art to the present invention.

What is claimed is:

1. A sensor for near-zone tissue characterization, comprising:
   a broad-band resonator, configured to be placed proximally to an edge of a tissue for characterization, without penetrating the tissue, the broad-band resonator comprising a conductive structure associated with a diameter-equivalent dimension D, in a plane substantially parallel with the edge, and with a feature size d, which is substantially equal to a spacing between conductive materials of the conductive structure; and
   at least one conductive lead, for providing communication with an external system,
   wherein the broad-band resonator is designed with $\Delta f/f$ of at least ±15%, $\Delta f$ being a range of frequencies for which there is a change of at least 10% in the reflection coefficient amplitude of a reflection signal of the resonator, and f a corresponding resonant frequency, the resonator being configured to resonate at a frequency which corresponds to a free-air wavelength range of between about $\lambda$ and about $40\lambda$, wherein $\lambda$ is at least about ten times the diameter-equivalent D,
   and wherein upon receiving a signal in the range of between about $\lambda$ and about $40\lambda$, the sensor is configured to induce electric and magnetic fields in the near zone in the tissue, the near zone being a generally disk-like region, delimited by a diameter of about D and a depth of penetration being limited to the feature size d,
   so that the tissue in the near zone effectively functions as part of the broad-band resonator, influencing its resonating values, such that the tissue in the near zone is thereby characterized through its electromagnetic properties, by the resonating response of the broad-band resonator.

2. The sensor of claim 1, wherein feature size d is between about 1/10 and 1/20 of the diameter-equivalent D.

3. The sensor of claim 1, wherein the resonator further comprises an electronic support structure.

4. The sensor of claim 1, wherein the resonating response is selected from the group consisting of a reflection coefficient amplitude of a reflection signal and a reflection coefficient phase of a reflection signal.

5. The sensor of claim 1, wherein the resonator is configured to respond to a range selected from the group consisting of at least about ±50% around a resonance value, and at least about ±25% around a resonance value.

6. The sensor of claim 1, and further including a connector to a transmission line, the connector providing substantial impedance matching between the sensor and the transmission line.

7. The sensor of claim 1, and further including a connection structure, associated with the connector, for providing a capability selected from the group consisting of a tuning capability, a switching capability, and a replacement capability, to components of the connector, for interchangeably optimizing the sensor to different applications.

8. The sensor of claim 1, formed as a construction, selected from the group consisting of:
   a thin, flexible construction,
   a thin, flexible construction, adapted for operation when attached to a hollow housing,
   a thin, flexible construction, adapted for operation when attached to a housing, filled with an electrically insulating material,
   a thin, flexible construction, adapted for operation when inserted into a hollow housing, and
   a thin, flexible construction, adapted for operation when inserted into a housing, filled with an electrically insulating material.

9. The sensor of claim 1, wherein the conductive structure is formed in a manner selected from the group consisting of:
   as a substantially flat spiral, and
   as two substantially flat spirals, wound together.

10. The sensor of claim 9, formed as a thin, flexible construction, adapted for operation in a manner selected from the group consisting of:
    when attached to a housing, and
    when inserted into a housing,
    wherein the conductive structure bends to form a proximal top to the housing.

11. The sensor of claim 1, wherein the conductive structure is formed as a conical helix.

12. The sensor of claim 11, and further including a tubular wall of a conductive material, extending proximally towards the tissue, to form an open cavity, selected from the group consisting of:
   a conical open cavity, and
   a cylindrical open cavity.

13. The sensor of claim 12, wherein the near zone is contained within the open cavity.

14. The sensor of claim 11, configured to be deposited on a funnel-shaped substrate.

15. The sensor of claim 1, wherein the conductive structure is formed as two combs, inserted into each other.

16. The sensor of claim 1, wherein the conductive structure is selected from the group consisting of:
   a conductive structure deposited over a self-supporting substrate,
   a conductive structure, deposited over a thin substrate and placed over a housing which forms a hollow region, and
   a conductive structure, deposited over a thin substrate and placed over a housing, which is formed of an electrical insulator.

17. The sensor of claim 1, wherein the conductive structure is formed of two parts, a substantially flat spiral and a helix, and further wherein the two parts are connected in a manner selected from the group consisting of in parallel and in series.

18. The sensor of claim 1, wherein the conductive structure is coupled in a manner selected from the group consisting of:
   inductively coupled,
   capacitively coupled,
   inductively and capacitively coupled, and
   resistively coupled.

19. The sensor of claim 1, wherein the D is between about 3 and about 25 mm.

20. The sensor of claim 1, wherein the resonator is configured to resonate at a frequency which corresponds to a free-air wavelength range selected from the group consisting of between about $\lambda$ and about 10$\lambda$, between about 10$\lambda$ and about 20$\lambda$, between about 20$\lambda$ and about 30$\lambda$, and between about 30$\lambda$, and about 40$\lambda$.

21. The sensor of claim 1, wherein in a far zone, the sensor has a radiation efficiency of less than 0.1%, for the free-air wavelength range of between about $\lambda$ and about 40$\lambda$.

22. The sensor of claim 1, configured to be sensitive to suspicious object sizes of at least about 0.25 mm in diameter.

23. A system for tissue characterization, comprising:
   a sensor for near-zone tissue characterization, which comprises:
      a broad-band resonator, configured to be placed proximally to an edge of a tissue for characterization, without penetrating the tissue, the broad-band resonator comprising a conductive structure associated with a diameter-equivalent dimension D, in a plane substantially parallel with the edge, and with a feature size d, which is substantially equal to a spacing between conductive materials of the conductive structure; and
      at least one conductive lead, for providing communication with an external system,
      wherein the broad-band resonator is designed with $\Delta f/f$ of at least $\pm 15\%$ $\Delta f$ being a range of frequencies for which there is a change of at least 10% in the reflection coefficient amplitude of a reflection signal of the resonator, and f a corresponding resonant frequency, the resonator being configured to resonate at a frequency which corresponds to a free-air wavelength range of between about $\lambda$ and about 40$\lambda$, wherein $\lambda$ is at least about ten times the diameter-equivalent D,
      and wherein upon receiving a signal in the range of between about $\lambda$ and about 40$\lambda$, the sensor is configured to induce electric and magnetic fields in the near zone in the tissue, the near zone being a generally disk-like region, delimited by a diameter of about D and a depth of penetration limited by the feature size d,
   so that the tissue in the near zone effectively functions as part of the broad-band resonator, influencing its resonating values,
   and so the tissue in the near zone is thereby characterized through its electromagnetic properties, by the resonating response of the broad-band resonator,
   the system further comprising the external signal-generation-control-and-analysis system, in communication with the sensor, via the at least one conductive lead.

24. A method of tissue characterization, comprising:
providing a sensor for near-zone tissue characterization, which comprises:
   a broad-band resonator, configured to be placed proximally to an edge of a tissue for characterization, without penetrating the tissue, the broad-band resonator comprising a conductive structure associated with a diameter-equivalent dimension D, in a plane substantially parallel with the edge, and with a feature size d, which is substantially equal to a spacing between conductive materials of the conductive structure; and
   at least one conductive lead, for providing communication with an external system,
   wherein the broad-band resonator is designed with $\Delta f/f$ of at least $\pm 15\%$, $\Delta f$ being a range of frequencies for which there is a change of at least 10% in the reflection coefficient amplitude of a reflection signal of the resonator, and f a corresponding resonant frequency, is the resonator being and is configured to resonate at a frequency which corresponds to a free-air wavelength range of between about $\lambda$ and about 40$\lambda$, wherein $\lambda$ is at least about ten times the diameter-equivalent D,
   and wherein upon receiving a signal in the range of between about $\lambda$ and about 40$\lambda$, the sensor is configured to induce electric and magnetic fields in the near zone in the tissue, the near zone being a generally disk-like region, delimited by a diameter of about D and a depth of penetration limited by the feature size d,
   so that the tissue in the near zone effectively functions as part of the broad-band resonator, influencing its resonating values,
   and so the tissue in the near zone is thereby characterized by its electromagnetic properties, by the resonating response of the broad-band resonator,
providing the sensor with sweeping signals within the range of between about $\lambda$ and about 40$\lambda$, thus inducing electric and magnetic fields, in the near zone, in the tissue;
recording the resonating response of the resonator, as a function of the sweeping signals; and
characterizing the tissue by the resonating response.

25. A sensor for near-zone tissue characterization, comprising:
   a broad-band resonator, configured to be placed proximally to an edge of a tissue for characterization, without penetrating the tissue, the broad-band resonator comprising a conductive structure associated with a diameter-equivalent dimension D, in a plane substantially parallel with the edge, and with a feature size d, which is substantially equal to a spacing between conductive materials of the conductive structure; and at least one conductive lead, for providing communication with an external system, wherein the broad-band resonator is designed with $\Delta f/f$ of at least $\pm 15\%$, $\Delta f$ being a range of frequencies for which there is a change of at least 10% in the reflection coefficient amplitude of a reflection signal of the resonator, and f a corresponding resonant frequency, f lying between 100 MHz and 350 MHz, the resonator being configured to resonate at a frequency which corresponds to a free-air wavelength range of between about $\lambda$ and about $40\lambda$, wherein $\lambda$ is at least about ten times the diameter-equivalent D, and wherein upon receiving a signal in the range of between about $\lambda$ and about $40\lambda$, the sensor is configured to induce electric and magnetic fields in the near zone in the tissue, so that the tissue in the near zone effectively functions as part of the broad-band resonator, influencing its resonating values, such that the tissue in the near zone is thereby characterized through its electromagnetic properties, by the resonating response of the broadband resonator.

26. A sensor for near-zone tissue characterization, comprising:

a broad-band resonator, configured to be placed proximally to an edge of a tissue for characterization, without penetrating the tissue, the broad-band resonator comprising a conductive structure associated with a diameter-equivalent dimension D, in a plane substantially parallel with the edge, and with a feature size d, which is substantially equal to a spacing between conductive materials of the conductive structure; and at least one conductive lead, for providing communication with an external system, wherein the broad-band resonator is designed with $\Delta f/f$ of at least $\pm 15\%$, $\Delta f$ being a range of frequencies for which there is a change of at least 10% in the reflection coefficient amplitude of a reflection signal of the resonator, and f a corresponding resonant frequency, the resonator being configured to resonate at a frequency which corresponds to a free-air wavelength range of between about $10\lambda$ and about $30\lambda$, wherein $\lambda$ is at least about ten times the diameter-equivalent D, and wherein upon receiving a signal in the range of between about $\lambda$ and about $40\lambda$, the sensor is configured to induce electric and magnetic fields in the near zone in the tissue, so that the tissue in the near zone effectively functions as part of the broad-band resonator, influencing its resonating values, such that the tissue in the near zone is thereby characterized through its electromagnetic properties, by the resonating response of the broadband resonator.

* * * * *